US010407685B2

(12) United States Patent
Adams, Jr. et al.

(10) Patent No.: US 10,407,685 B2
(45) Date of Patent: Sep. 10, 2019

(54) METHODS FOR IMPROVING COMPETENCY OF PLANT CELLS

(75) Inventors: Whitney R. Adams, Jr., Mystic, CT (US); Brian J. Martinell, Mount Horeb, WI (US); Jyoti R. Rout, Ballwin, MO (US); Edward J. Williams, Madison, WI (US)

(73) Assignee: Monsanto Technology LLC, St. Louis, MO (US)

( * ) Notice: Subject to any disclaimer, the term of this patent is extended or adjusted under 35 U.S.C. 154(b) by 413 days.

(21) Appl. No.: 13/328,222

(22) Filed: Dec. 16, 2011

(65) Prior Publication Data

US 2012/0156784 A1 Jun. 21, 2012

Related U.S. Application Data

(60) Provisional application No. 61/424,136, filed on Dec. 17, 2010.

(51) Int. Cl.
*C12N 15/82* (2006.01)

(52) U.S. Cl.
CPC ................. *C12N 15/8205* (2013.01)

(58) Field of Classification Search
CPC ...... A01H 5/10; C12N 15/00; C12N 15/8205; C12N 15/8207
USPC ......... 800/294, 312, 320, 320.1, 320.3, 314, 800/320.2; 47/58.1
See application file for complete search history.

(56) References Cited

U.S. PATENT DOCUMENTS

| | | | |
|---|---|---|---|
| 5,508,184 A | 4/1996 | Negrutiu et al. | |
| 5,591,616 A | 1/1997 | Hiei et al. | |
| 5,770,450 A * | 6/1998 | Shillito et al. | 435/424 |
| 5,824,877 A | 10/1998 | Hinchee et al. | |
| 5,981,840 A | 11/1999 | Zhao et al. | |
| 6,384,301 B1 | 5/2002 | Martinell et al. | |
| 6,403,865 B1 * | 6/2002 | Koziel et al. | 800/302 |
| 6,603,065 B2 | 8/2003 | Paszkowski et al. | |
| 7,297,838 B2 * | 11/2007 | Chen et al. | 800/294 |
| 7,402,734 B2 | 7/2008 | Martinell et al. | |
| 7,560,611 B2 | 7/2009 | Adams et al. | |
| 7,682,829 B2 | 3/2010 | Cai et al. | |
| 7,888,552 B2 | 2/2011 | Ye et al. | |
| 7,939,325 B2 | 5/2011 | Adams et al. | |
| 8,030,544 B2 | 10/2011 | Martinell et al. | |
| 8,044,260 B2 | 10/2011 | Dersch et al. | |
| 8,357,834 B2 | 1/2013 | Martinell et al. | |
| 8,362,317 B2 * | 1/2013 | Calabotta | A01H 4/003 800/278 |
| 8,466,345 B2 | 6/2013 | Martinell et al. | |
| 8,581,035 B2 | 11/2013 | Rout | |
| 8,815,596 B2 | 8/2014 | Adams et al. | |
| 8,847,009 B2 | 9/2014 | Rout | |
| 8,872,000 B2 | 10/2014 | Martinell et al. | |
| 9,006,513 B2 | 4/2015 | Calabotta et al. | |

| | | | |
|---|---|---|---|
| 2003/0093829 A1 | 5/2003 | Chen et al. | |
| 2005/0278802 A1 * | 12/2005 | Wilson et al. | 800/278 |
| 2006/0130185 A1 | 6/2006 | Chang et al. | |
| 2009/0324797 A1 | 12/2009 | Bobzin et al. | |
| 2013/0160157 A1 | 6/2013 | Ye et al. | |
| 2015/0017644 A1 | 1/2015 | Rout | |
| 2015/0040266 A1 | 2/2015 | Ye et al. | |
| 2015/0082497 A1 | 3/2015 | Adams et al. | |
| 2015/0113683 A1 | 4/2015 | Martinell et al. | |

FOREIGN PATENT DOCUMENTS

| | | |
|---|---|---|
| JP | S60-251887 | 12/1985 |
| JP | S63-160588 | 7/1988 |
| JP | 3038479 | 5/2000 |
| JP | 3125050 | 1/2001 |
| WO | WO 2002/031113 | 4/2002 |
| WO | WO 2003/041491 | 5/2003 |
| WO | WO 2006/004914 | 1/2006 |
| WO | WO 2011/068468 | 6/2011 |

OTHER PUBLICATIONS

Abdel-Rahman et al. Maize tissue culture plant regeneration ability can be improved by polyethylene glycol treatment. In Vitro Cell. Dev. Biol.—Plant (2010) 46: 509-515.*
Brettschneider et al. Efficient transformation of scutellar tissue of immature maize embryos. Theor Appl Genet (1997) 94: 737-748.*
Langhansova et al. Polyethylene glycol and abscisic acid improve maturation and regeneration of Panax ginseng somatic embryos. Plant Cell Rep. (2004) 22: 725-730.*
Murray. Priming sweet corn to improve emergence under cool conditions. HortScience 25(2): 231, 1990.*
Chen et al. High frequency of plant regeneration from anther culture in flax, *Linum usitatissimum* L. Plant Breeding 117, 463-467 (1998).*
Duncan et al. The production of callus capable of plant regeneration from immature embryos of numerous Zea mays genotypes. Planta (1985) 165:322-332.*
Murray. Priming sweet corn seed to improve emergence under cool conditions. HortScience 25(2):231 (1990).*
Vain et al. Osmotic treatment enhances particle bombardment-mediated transient and stable transformation of maize. Plant Cell Reports (1993) 12:84-88.*

(Continued)

*Primary Examiner* — June Hwu
(74) *Attorney, Agent, or Firm* — Dentons US LLP; David Lanzotti, Esq.

(57) ABSTRACT

The present invention provides methods for improving competency of plant cells for bacterial-mediated transformation comprising contacting the plant cells with an effective amount of polyethylene glycol (PEG) for a period of time prior to transformation. The ability to store and maintain competent plant cells for transformation and tissue culture allows more efficient planning and execution of large-scale experiments by providing flexibility of peak production hours, or during unplanned disruptions in the production process. These methods are useful in preserving the viability of plant cells in various storage conditions, thus improving their competency for transformation and tissue culture.

8 Claims, 3 Drawing Sheets

(56) References Cited

OTHER PUBLICATIONS

Hongbo et al. Impacts of PEG-6000 pretreatmetn for barley (*Hordeum vulgare* L.) seeds on the effect of their mature embryo in vitro culture and primary investigation on its physiological mechanism. Colloids and Surfaces B: Biointerfaces 41 (2005) 73-77.*
U.S. Appl. No. 13/873,092, filed Apr. 29, 2013, Chen et al.
U.S. Appl. No. 14/642,671, filed Mar. 9, 2015, Calabotta et al.
U.S. Appl. No. 14/550,694, filed Nov. 21, 2014, Duncan et al.
Broothaerts et al., "Gene transfer to plants by diverse species of bacteria," *Nature* 433:629-633, 2005.
Deng et al., "Moderate desiccation dramatically improves shoot regeneration from maize (*Zea mays* L.) callus," *In Vitro Cell Day Biol—Plant* 45(1):99-103, 2009.
International Search Report for PCT/US2011/065420, dated Apr. 5, 2012. 5 pp.
Money, "Osmotic pressure of aqueous polyethylene glycols," *Plant Phys* 91:766-769, 1989.
Supplementary European Search Report for EP 11 84 9811, dated Feb. 4, 2014. 4 pp.
Walker et al., "Effect of polyethylene glycol and sugar alcohols on soybean somatic embryo germination and conversion," *Plant Cell Tissue and Organ Culture* 64:55-62, 2001.
Japanese Office Action regarding Application No. 2013-544815, dated Sep. 29, 2015 (English translation). 3 pp. /JH/.
KARAMI, "Factors Affecting Agrobacterium-mediated Transformation of Plants," Transgenic Plant Journal 2(2), 127-137, 2008.

\* cited by examiner

METHODS FOR IMPROVING COMPETENCY OF PLANT CELLS

CROSS REFERENCE TO RELATED APPLICATION

This application claims the benefit of priority to U.S. Provisional Application Ser. No. 61/424,136, filed on Dec. 17, 2010. The entire disclosure of the above application is incorporated herein by reference.

FIELD OF THE INVENTION

This invention is in the field of plant biotechnology. More specifically, a method of improving competency of plants cells for bacterial-mediated transformation is provided.

BACKGROUND OF THE INVENTION

Plant tissues such as embryos can be obtained in large quantities by mechanical means, as disclosed in U.S. Pat. No. 7,427,695, for use in tissue culture. Typically, once such plant tissues are obtained, they are used immediately or within hours in tissue culture processes with or without a transformation step. When stored for later use, its competency for transformation may be reduced. Embryonic axes derived from dry seeds, for example as disclosed in U.S. Patent Application Publication No. 2008/0280361, are relatively stable upon storage, but a hydration step prior to transformation may reduce their competency for transformation.

SUMMARY OF THE INVENTION

The present invention provides methods for improving competency of plant cells for bacterial-mediated transformation comprising contacting the plant cells with an effective amount of polyethylene glycol prior to transformation.

In certain embodiments, the effective amount of polyethylene glycol may be from about 1% to about 25% by volume. In more particular embodiments, the effective amount of polyethylene glycol is about 20% by volume.

The molecular weight of the polyethylene glycol may range from about 200 to about 10000, while in more particular embodiments the molecular weight of the polyethylene glycol is from 4000 to 8000.

In certain aspects, the composition further comprises an effective amount of at least one growth regulator, wherein the growth regulator comprises an amount of auxin, cytokinin, or combination thereof. Auxins may include IAA, 2,4-D, NAA, IBA, dicamba, or a combination thereof, and the amount of auxin is preferably from about 0.001 mg/L to about 30 mg/L.

The cytokinins may comprise BAP, zeatin, kinetin, TDZ, or a combination thereof, and may be present in an amount from about 0.001 mg/L to about 30 mg/L.

In practicing the present invention, the period of time for contacting the plant cells with PEG may be from 1 day to about 30 days. In other more specific embodiments, the effective period of time is about 3 days to 7 days. In still other embodiments, plant cells are contacted with the PEG for a period of about 30 min to 300 min.

The methods of present invention may further comprise a rinse step, wherein the plant cells that have been contacted with the PEG are rinsed with a non-PEG containing composition prior to transformation.

Another aspect of the present invention further comprises regenerating the plant cells. The plant cells may comprise cells of seed, leaf, stem, root, immature embryo, mature embryo, callus, microspore, meristem, cotyledon, hypocotyl, epicotyl, mesocotyl, coleoptiles, radical, plumule or reproductive tissue from a monocotyledenous or dicotyledenous plant species.

In practicing the methods of the present invention, the bacterial mediated transformation may be Agrobacterium-mediated, or Rhizobium-mediated transformation.

A transgenic plant, and any plant parts thereof as defined elsewhere in the present disclosure, created using the methods of the present invention disclosed herein, is also an aspect of the present invention.

BRIEF DESCRIPTION OF THE DRAWINGS

The accompanying drawings, which are incorporated in and form a part of the specification, illustrate the embodiments of the present invention and together with the description, serve to explain the principles of the invention. In the drawings.

DETAILED DESCRIPTION OF THE INVENTION

Figure 1:
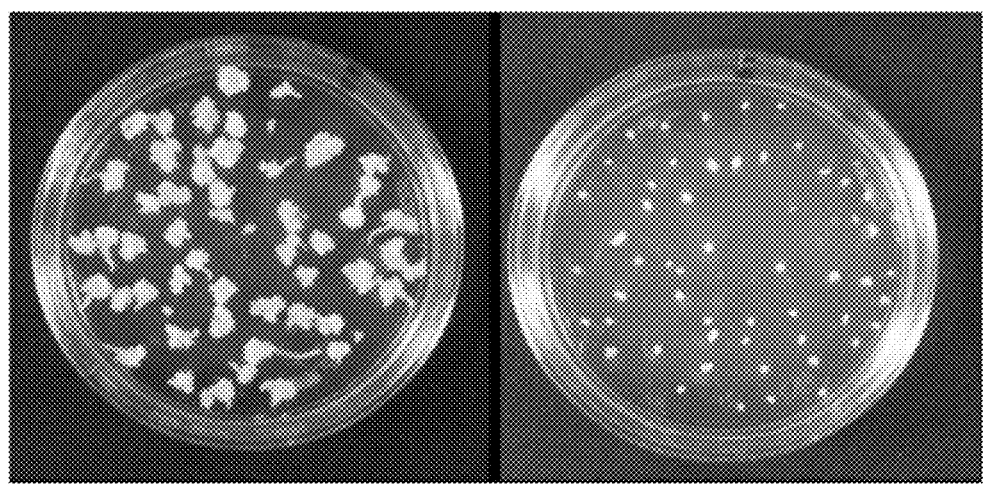
FIG. 1 illustrates callus production from embryos that were stored in Lynx 2304 medium supplemented with PEG (left panel), compared to embryos that were stored in Lynx 2304 without PEG (right panel).

The following is a detailed description of the invention provided to aid those skilled in the art in practicing the present invention. Those of ordinary skill in the art may make modifications and variations in the embodiments described herein without departing from the spirit or scope of the present invention. Unless defined otherwise, all technical and scientific terms used herein have the same meaning as commonly understood by one of ordinary skill in the art to which this invention belongs. Generally, the nomenclature and descriptions of basic manufacture or laboratory procedures described herein are known and commonly employed in the art. Unless otherwise noted, conventional methods are used for these procedures, and are exemplified by a variety of general technical dictionaries or texts. Where a term is provided in the singular, the inventors also contemplate aspects of the invention described by the plural of that term. The inventors do not intend to be limited to a particular mechanism or mode of action. Reference thereto is provided for illustrative purposes only. All publications, patent applications, patents, and other references mentioned herein are expressly incorporated by reference in their entirety.

The present invention provides methods for improving competency of plant cells for bacterial-mediated transformation comprising contacting (applying, treating, storing, touching, joining, mixing, or to otherwise cause interaction) the plant cells with an effective amount of polyethylene glycol (PEG) for a period of time prior to transformation sufficient to enhance transformation of the so-treated tissue.

The methods of the present invention are useful in preserving the viability of plant cells in corn immature embryos during various storage conditions, thus improving their competency for transformation and tissue culture compared with tissues that are not contacted with an effective amount of PEG. Hence, an "effective amount" of the composition, is defined as an amount that is efficacious for improving competency for bacterial-mediated transformation of plant cells that are contacted by the composition, as compared to plant cells that are contacted by either none, too little, or too much of the composition so as to either be ineffectual, or detrimental to the plant cells' competency.

The ability to store and maintain competent plant cells for transformation and tissue culture allows more efficient planning and execution of large-scale experiments by providing flexibility of peak production hours, or during unplanned disruptions in the production process. This also enables greater flexibility for shipping tissues to different sites. Also, such methods are useful in improving competency of plant cells in embryonic axes from dry seed, for example, of soybean for transformation.

In order to provide a clear and consistent understanding of the specification and the claims, including the scope given to such terms, the following definitions are provided.

The term "competency" is defined as a response of a plant cell to tissue culture or transformation. A "response" is typically defined in biological systems as any behavior or change of a living organism that results from an external or internal stimulus. Hence, the term "improved competency" is defined as enhancement over a basal or negative response to tissue culture or transformation. In some aspects, the improved competency to tissue culture may be measured by a higher rate of survivability of the plant cells. In other aspects, improved competency to transformation is measured as an increase in transformation frequency.

The term "plant cells" generally refers to any cells from any part of a plant, including but not limited to seed, leaf, stem, root, immature embryo, mature embryo, callus, microspore, meristem, cotyledon, hypocotyl, epicotyl, mesocotyl, coleoptiles, radical, plumule or flower cells including sepal, petal, stamen, pollen, pollen tube, pistil, receptacle, and ovule, among others. The plant cells may be derived from essentially any plant, including but not limited to barley, corn, oat, rice, rye, sorghum, turf grass, sugarcane, wheat, alfalfa, banana, broccoli, bean, cabbage, canola, carrot, cassava, cauliflower, Chinese cabbage, celery, citrus, clover, coconut, coffee, cotton, a cucurbit, Douglas fir, dry bean eggplant, eucalyptus, fennel, flax, garden beans, garlic, gourd, grape, olive, okra, onion, leek, loblolly pine, melon, palm, lettuce, pea, peanut, pepper, potato, poplar, pine, pumpkin, radish, sunflower, safflower, sorghum, soybean, spinach, squash, strawberry, sugar beet, sweet gum, sweet potato, switch grass, tea, tobacco, tomato, triticale, turf grass, watermelon, ornamental, shrub, nut, chickpea, pigeon pea, millet, hops, and pasture grass plants.

"Embryo" is part of a seed, comprising precursor tissues (meristematic tissues) for the leaves, stem, and root. Once the embryo begins to grow (germinate), it becomes a seedling plant.

"Meristem" or "meristematic tissue" comprises undifferentiated cells, the meristematic cells, which differentiate to produce multiple plant structures including stem, roots, leaves, germline tissue and seeds "Explant" is a term used to refer to target material for transformation comprising plant cells. The plant cells are defined as above.

The method of the present invention comprises contacting the plant cells with an effective amount of polyethylene glycol (PEG) for a period of time prior to transformation. Percent amounts of PEG described herein are given by volume. In certain non-limiting embodiments, the PEG may be dissolved in sterile distilled water (SDW), Inoculation medium (INO, see Table 7), or Bean Germination Medium (BGM, see Table 8). The effective amount of PEG of the present invention can vary depending on the crop and is generally in the range of about 1% to about 50%, including about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50% and specifically including all ranges derivable between any two such values. In certain non-limiting embodiments, the average molecular weight of the PEG may be from about 200 and about 35000, including about 200, 300, 400, 550, 600, 1000, 1500, 2000, 3000, 3350, 4000, 6000, 8000, 10000, 20000, and 35000 and specifically including all ranges derivable between any two such values. In some embodiments, the molecular weight of PEG is 4000, 5000, 6000, 7000, or 8000.

In some aspects of the present invention, the plant cells may be contacted with a composition comprising an effective amount of PEG, and one or more plant growth regulators (PGRs). Embryogenic culture response is the product of interactions among genotype, developmental stage of the explant, culture conditions and growth regulator composition of the culture medium. During the process of culture initiation, an explant undergoes a process known as "de-differentiation"—a step in which the original developmental stage of the explants is suitably modified with the aid of growth regulators. Depending on the effectiveness of the growth regulators, this process may take hours or days, where delivering the optimum amount of growth regulator combination(s) is a key step. One significant hurdle in this key step of delivering "growth regulators" is that a very high dose of growth regulators may cause deleterious effects to the explant. One aspect of the present invention provides a method to contact explants with a high concentration of PGRs prior to culturing on a suitable culture medium without deleterious effects by combining the PGRs in a composition of PEG. This approach not only mitigates deleterious effect of high concentrations of growth regulators, but also enhances the de-differentiation process of plant cells.

Many PGRs are known in the art and could be used according to the methods of the present invention, such as auxins, including but not limited to 4-CPA, 2,4-Dichloro-phenoxyacetic acid (2,4-D), dichlorprop, fenoprop, indole-3-acetic acid (IAA), indole-3-butyric acid (IBA), naphthaleneacetamide, α-naphthaleneacetic acid, 1-naphthol naphthoxyacetic acid (NAA), potassium naphthenate, sodium naphthenate, and 2,4,5-trichlorophenoxy acetic acid, 3,6-dichloro-2-methoxybenzoic acid (dicamba), and 4-Amino-3,5,6-trichloropicolinic acid (picloram); antiauxins including but not limited to clofibric acid, and 2,3,5-triiodobenzoic acid; cytokinins including but not limited to 2iP, benzyladenine, thidiazuron (TDZ), 6-benzylaminopurine (BAP), kinetin, and zeatin; defoliants including but not limited to calcium cyanamide, dimethipin, endothal, ethephon, merphos, metoxuron, pentachlorophenol, and tribufos; ethylene inhibitors including but not limited to aviglycine, and 1-methylcyclopropene; ethylene releasers including but not limited to 1-aminocyclopropanecarboxylic acid, etacelasil, ethephon, and glyoxime; gibberellins including but not limited to gibberellic acid (GA3); herbicides including but not limited to glyphosate, glufosinate, DL-Phosphinothricin, 3,6-dichloro-2-methoxybenzoic acid, and 2,4-Dichlorophenoxyacetic acid; growth inhibitors and retardants including but not limited to abscisic acid, ancymidol, butralin, carbaryl, chlorphonium, chlorpropham, dikegulac, flumetralin, fluoridamid, fosamine, glyphosine, isopyrimol, jasmonic acid, maleic hydrazide, mepiquat, piproctanyl, prohydrojasmon, propham, 2,3,5-tri-iodobenzoic acid, chlormequat, daminozide, flurprimidol, mefluidide, paclobutrazol, tetcyclacis, and uniconazole; morphactins including but not limited to chlorfluren, chlorflurenol, dichlorflurenol, and flurenol; growth stimulators including but not limited to brassinolide, forchlorfenuron, and hymexazol; and/or other unclassified plant growth regulators including but not limited to benzofluor, buminafos, carvone, ciobutide, clofencet, cloxyfonac, cyanamide, cyclanilide, cycloheximide, cyprosulfamide, epocholeone, ethychlozate, ethylene, fenridazon, heptopargil, holosulf, inabenfide, karetazan, lead arsenate, methasulfocarb, prohexadione, pydanon, sintofen, triapenthenol, and trinexapac.

In certain embodiments of the present invention, the auxin is 2,4-D, and in other embodiments the auxin is picloram. In other embodiments the cytokinin is TDZ, and in still other embodiments the cytokinin is BAP.

One of skill in the art of plant cell culture and transformation would be able to determine appropriate levels and/or ratios of plant growth regulators that are suitable for use for a specific plant species with the present invention. For instance, levels of these or other PGRs with a functionally equivalent level of activity as, for instance, BAP and/or 2,4-D in corn or in another plant species, may be determined by varying the levels of such growth regulators present in media to which explants are contacted, and monitoring the growth of the explants and tissues derived therefrom. Thus, if other PGRs are used, they would nevertheless comprise a plant growth-regulatory effect equivalent to these contemplated amounts and ratios of the above listed PGRs.

In various non-limiting embodiments, the amount of PGRs used in the PEG-containing composition may range from 0.001 mg/L to about 30 mg/L, including about 0.01, 0.1, 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30 mg/L, and specifically including all ranges derivable between any two such values.

In certain non-limiting embodiments, immature corn embryo explants are contacted with the PEG-containing composition for a period of about 1 to 10 days, including about 2, 3, 4, 5, 6, 7, 8, 9, and 10 days, and specifically including all ranges derivable between any two such values. In a specific embodiment, the explants are contacted with the composition for about 3 days.

In other embodiments, mature soy embryo explants comprising cells are contacted with a PEG-containing composition for a period of about 30 to 300 minutes, including about 30, 40, 50, 60, 70, 90, 100, 120, 180, 240, and 300 minutes, and specifically including all ranges derivable between any two such values. In a specific embodiment, the explants are contacted with the composition for about 60 minutes.

In still other non-limiting embodiments, the explants are contacted with the PEG-containing composition at a temperature from about 2 to 30 degrees Celsius, including about 3, 4, 5, 6, 7, 8, 9, 10, 11, 12, 13, 14, 15, 16, 17, 18, 19, 20, 21, 22, 23, 24, 25, 26, 27, 28, 29 and 30 degrees Celsius, and specifically including all ranges derivable between any two such values.

The ranges of amount, duration, temperature, and molecular weight disclosed herein are non-limiting. Those of ordinary skill in the art could carry out the present invention using an amount, duration, temperature or molecular weight below, above, or in between those specifically given, without departing from the scope and spirit of the present invention, depending upon the specific requirements of a particular plant species.

The methods of present invention may further comprise a rinse step, wherein the plant cells which have been contacted with the polyethylene glycol composition are rinsed with a non-PEG containing composition prior to transformation. In various non-limiting aspects, the non-PEG containing composition may be water, or a medium such as ½ MS PL (Table 1), ½ MS VI (Table 2), INO (Table 6), BGM (Table 8), or *Agrobacterium* culture re-suspension, described elsewhere in the present disclosure. In certain non-limiting embodiments, the rinse step may comprise one or more rapid repetitious rinses with the desired rinse medium, or may alternatively comprise a single rinse for a longer duration of 1 to 5 minutes.

TABLE 1

½ MS PL Medium Composition.

| Ingredient | Source | Amount per liter |
|---|---|---|
| MS Basal Salts | Phytotech M524 | 2.165 g |
| MS Vitamins | Phytotech M533 | 103.1 mg |
| Glucose | Phytotech G386 | 36 g |
| Sucrose | Phytotech S391 | 68.5 g |
| Proline | Fisher BP392-100 | 0.115 g |
| pH to 5.4 | | |

TABLE 2

½ MS VI Medium Composition.

| Ingredient | Source | Amount per liter |
|---|---|---|
| MS Basal Salts | Phytotech M524 | 2.165 g |
| MS Vitamins | Phytotech M533 | 103.1 mg |
| Glucose | Phytotech G386 | 10 g |
| Sucrose | Phytotech S391 | 20 g |
| Proline | Sigma P-5607 | 0.115 g |
| pH to 5.4 | | |

In certain non-limiting aspects of the present invention, the plant cells may be immature embryos. When the immature embryos are of a monocot such as corn, the tissues to be substantially isolated are provided in any suitable manner, for example attached to the ear or head on which the seeds mature. Monocot seeds may be removed from the ear or head prior to substantially purifying the target tissue. Ears are typically collected 10-12 days post pollination and surface sterilized. Methods for surface sterilization are well known in the art, and include, but are not limited to, immersion in a solution containing an effective concentration of ethanol, or sodium hypochlorite for an effective period of time, for example from 1 to 15 minutes. Immature embryos may be obtained by any suitable technique, including manually, or by mechanized or automated methods.

An opening in the pericarp or seed coat of the monocot seeds is provided to effectuate isolation of the desired explant. This may be accomplished by any suitable technique, such as, but not limited to, making a hole, puncture, or incision with a needle, awl, blade, or other suitable implement. In some applications of the method, no pericarp tissue need be removed; in other applications, the opening of the pericarp may include removal of at least part of the pericarp and possibly of some non-embryo tissue (e.g., endosperm). Preferably, the opening is sufficient to substantially separate the embryo from the seed, which may be done in manually, by using a sterile tool such as a spatula to scoop out the endosperm and embryo, or by pushing on the side of the kernel, causing the embryo to emerge and be partially or completely exposed from the kernel. It may be necessary only to weaken the pericarp sufficiently (for example, by abrasion, or by other physical, chemical, or enzymatic treatment) so that application of force to the seed results in substantial isolation of the target tissue, such as the embryo.

Methods of obtaining immature embryos by automated or mechanized means are disclosed in U.S. Pat. No. 7,560,611. The method includes the step of applying force to the seeds sufficient to substantially isolate the target tissue, such as an immature embryo, from the seeds, wherein the substantially isolated target tissue is suitable for genetic transformation and tissue culture. Force may be applied to multiple seeds consecutively or simultaneously. The applied force can be continuous or non-continuous (for example, pulsed or wave-like force), and is generally mechanically applied, that is to say, the force is obtained through the use of a device or machine rather by human hand. The amount of force applied is preferably sufficient to overcome the adhesion of the target (e.g., embryo) and non-target (e.g., non-embryo tissue such as endosperm) from each other, thus allowing separation of the target and non-target tissues. Any suitable force or forces may be employed for removal of the target tissue from its seed, and multiple forces may be used in combination, sequentially or simultaneously. Suitable forces include, but are not limited to, fluid jet positive pressure, liquid jet positive pressure, mechanical positive pressure, negative pressure, aspiration, centrifugal force, linear acceleration, linear deceleration, fluid shear, fluid turbulent flow, and fluid laminar flow. Fluid forces can be exerted by any fluid, gases or liquids or combinations of both.

The method can further include the step of separating the substantially isolated target tissue, such as immature embryos, from associated non-embryo tissue such as endosperm, glumes, and seed coat or pericarp tissues. Methods for separating immature embryos from other tissues are described in US Patent Application Publication No. 2009/0142837. Separation may be accomplished by one or more suitable techniques, including, but not limited to, separation by size exclusion (for example, by filtration in one or more filtering steps), separation based on hydrophobicity, hydrophilicity, lipophilicity, or other attractive forces, and separation by mass or density differentials (for example, separation by centrifugation, settling, and decanting). The separation step or steps can be optional, for example, where no additional isolation of intact or partial embryos is necessary for their use in tissue culture.

These methods to provide the substantially isolated target tissues, such as corn embryos, that are suitable for genetic transformation or tissue culture can be automated, for example by employing robotic or mechanical handling of the corn ears or seeds, opening of the pericarp, application of force to the seed, or the optional separation steps. Such automation may use optical or mechanical sensors to aid in positioning the corn ears or seeds relative to the applied force or forces, or in the separation steps. An apparatus for substantially isolating corn embryos is provided as disclosed in U.S. Pat. No. 7,560,611 that comprises at least one aperture for guiding a fluid stream, wherein the fluid stream contacts kernels on the corn ear and substantially isolates embryos from the kernels. Generally, it is preferred that the fluid stream contact as many of the kernels in a given period of time as is convenient, so as to more rapidly isolate embryos. The at least one aperture can include a single aperture or multiple apertures (for example, single or multiple nozzles, which can include flat, round, oval, fan-shaped or other patterned nozzles, and adjustable, moving, or stationary nozzles), and can generate a fluid flow of any suitable type and medium. Fluids may be gases (such as air, nitrogen, or gas mixtures), liquids (such as water, physiological saline, or various culture media), or combinations. Suitable fluid flows include, but are not limited to, fluid jets (such as single or multiple columnar jets; flat, cone-shaped, or fan-shaped jets or sprays; and sheet-like jets), laminar fluid flow, and turbulent fluid flow. Suitable fluid flows can result in one or more forces to remove the embryo from its kernel, including positive pressure or negative pressure or both. The one or more forces may be applied to multiple seeds consecutively or simultaneously, in a continuous or non-continuous manner, and is generally applied mechanically and not manually. Other suitable forces may be centrifugal force, linear acceleration, linear deceleration, and fluid shear. Such forces can be uniform or non-uniform, continuous or non-continuous (such as a pulsed or wave-like force) or in any combination thereof.

The apparatus may further include a means for moving the target tissue being substantially purified and the fluid stream, relative to each other. For example, either the ear of corn containing seeds or the fluid stream, or both, may be moved. Various embodiments of the apparatus can be used with single or multiple, intact or partial ears of corn. For example, the corn ear or ears can be secured to a holder or grasper, which is moved relative to the fluid stream. In other embodiments, however, the corn ear or ears need not be individually secured to a holder but can be freely movable so as to allow multiple kernels to be contacted by the force used to remove the embryos from the kernels. The means for moving at least one corn ear relative to the fluid stream can rotate the at least one corn ear and the at least one aperture relative to each other, or can move the fluid stream along the longitudinal axis of the at least one corn ear, or can provide any suitable three-dimensional movement of the at least one corn ear and the at least one aperture relative to each other, such as a combination of rotation and longitudinal motion.

The apparatus can further include at least one separator for separating target tissues from non-target tissues. For example, embryos may be separated from non-embryo tissues, wherein the separated embryos comprise at least some corn embryos suitable for genetic transformation or tissue culture. Separators can work by any suitable mechanism, including, but not limited to, separation by size exclusion (for example, using a mesh, screen, perforated surface, or other device capable of excluding objects of a certain size), separation based on hydrophobicity or other attractive forces (for example, using a material, solid or fluid, that can attract or repel the embryos), and separation by mass or density differentials (for example, using a centrifuge, or using solutions for differential settling). The separator can be optional, for example, where no additional isolation of intact or partial embryos is necessary for their use in genetic transformation or tissue culture.

The substantially isolated (and optionally separated) immature embryos include at least some embryos, such as immature intact or partial embryos, suitable for tissue culture applications, transformation, callus formation, direct embryogenesis, formation of differentiated plant tissue, formation of at least one mature plant, formation of at least one fertile mature plant, and combinations of these processes, as described above. The substantially isolated immature embryos and non-embryo tissues may also be used for other purposes, such as, but not limited to, genetic or biochemical analysis.

Combination apparatuses can optionally include a means for moving the at least one corn ear relative to the source or sources of force (that is to say, the solid surface for applying mechanical positive pressure, the aperture for guiding a fluid flow, or the aperture for applying negative fluid pressure). Preferably the ear or ears is moved relative to the source of force so that the force or forces contact as many of the kernels in a given period of time as is convenient, so as to more rapidly isolate embryos.

Combination apparatuses can further include at least one means for further separation of the substantially isolated immature embryos suitable for genetic transformation or tissue culture, wherein the separated embryos comprise at least some corn embryos suitable for genetic transformation or tissue culture. Separators can work by any suitable mechanism, including, but not limited to, separation by size exclusion, separation based on attractive forces, and separation by mass or density differentials.

In another aspect of the present invention, the plant cells are mature embryos. Mature embryo explants can be obtained from dry seed, for example as disclosed in U.S. Patent Application Publication No. 2008/0280361. These explants are referred to as dry-excised explants (DEEs). Dried wet explants may also be used, which are explants that have been excised from seed following hydration/imbibition, and are subsequently dehydrated and stored. Both of these types of explants have been shown to be fairly stable upon storage, but a rapid hydration step prior to transformation may reduce their competency for bacterial-mediated transformation. Although not intending to be bound by a particular mechanism of action, the methods of the present invention are useful in regulating the rate of hydration of embryonic explants derived from dry seed, or explants that are dehydrated following excision of hydrated, or imbibed seeds, thereby improving the competency of plant cells for bacterial-mediated transformation.

In various embodiments, explants comprising plant cells may be obtained by either manual or mechanical methods. Prior to embryo excision, seeds may be subjected to a sterilization step as well as a culling step, to avoid microbial contamination, to remove seeds with a high degree of bacterial or fungal contamination, and also to remove seeds that may for any reason be unlikely to produce viable explant tissue for use with the present invention. Culling may be carried out, for example, based on parameters such as the size, color, or density of the seed or other characteristics, including chemical composition characteristics. Examples of culling methods may include the use of an automatic scale after size sorting. An optical sorter suitable for this purpose is the Sortex 3000 Series Color Sorter (Buhler-Sortex K K, Yokohama, Japan). Other culling techniques may also be employed including culling by moisture content.

In specific embodiments, excision is mechanically performed using rollers that crush seeds applied to their faces, which can be counter-rotating. The gap between the rollers may be adjusted based on the size of the applied seeds. Roller material may, for instance, be elastomeric or metallic. In certain embodiments, stainless steel rollers have been found to retain beneficial working qualities even following repeated and sustained use. In one embodiment, an explant may have an internal moisture of about 3-25%, including about 3, 5, 6, 7, 8, 9, 10, 11, 12, 13, 14, 16, 17, 18, 19, 20, 21, 22, 23, 24, and 25% internal moisture, and specifically including all ranges derivable between any two such values. Seeds from which explants are to be prepared may be harvested at a predetermined internal moisture suitable for isolating transformable plant cells therefrom. Brittleness of seeds may be altered by manipulating moisture content, allowing for efficient splitting of seeds and preparation of explants. For instance, an internal moisture content such as 3% to 7% may be advantageous. Seeds may be held at such moisture contents or any other moisture content yielding stable storage conditions (and transformable explants) prior to use. Brittleness of seeds may also be altered by exposing the seeds to low temperatures, for example −20° C., or −80° C., or even colder, such as when contacted with liquid nitrogen (about −196° C.).

Dry explants of various ages may be used, including when explants are relatively "young" in that they have been removed from seeds for less than a day, for example, from about 1 to 24 hours, such as about 2, 3, 5, 7, 10, 12, 15, 20, or 23 hours prior to use. Explants may also be stored for longer periods, including days, weeks, months or even years, depending upon storage conditions used to maintain explant viability. Those of skill in the art in particular will understand that storage times may be optimized such that the quality and/or yield of transformants as well as the efficiency of the transformation process is maximized.

A dry seed or an explant may be first primed, for example, by imbibition of a liquid such as water or a sterilization liquid, before being redried, and later used for transformation and regeneration. The seed or the explant may also be primed by raising the internal seed moisture content to greater than 30%, holding the seed or the explant at a time point, and then re-initiating imbibition at a later time point. Alternatively, the seed or the explant may be primed by raising the internal moisture content to greater than 30%, storing the seed or the explant for a predetermined period, drying the seed or the explant to the internal moisture content of below 20%, and then re-initiating imbibition.

Regenerable transformable explants may be harvested that contain no, some, or a part of each cotyledon remaining attached to the embryonic tissue, for example as much as ¼ of the cotyledon. These explants are considered substantially similar, as they may each result in a stable transformed plant. The explant should however contain at least some of the meristematic region of the embryo such that typically the explant can produce a shoot within 12 weeks of the onset of tissue culture growth conditions.

A number of parameters for obtaining and handling explants may be varied. Sterilization may be performed by contacting a seed or explant with a liquid sterilizing agent. A seed or an explant may also be contacted with a gaseous sterilizing agent, or with an irradiating sterilizing agent such as UV light. Alternatively, a seed or an explant may be sterilized by subjecting the seed or the explant to a brief period of high temperatures so as to reduce the vigor of biological contaminants such as adventitious bacteria and fungi on the surface of the seed or the explant without reducing the vigor of the seed or the explant. This can be achieved at a temperature higher than 40° C., for example from about 40° C. to about 90° C. The temperature can be raised, for instance, by either forced heated air or steam. Such temperatures can be provided by dryers produced by Bry-Air Inc. (Sunbury, Ohio, USA). The addition of nystatin (50 ppm) and thiabendazole (10 ppm) dissolved in DMSO (1.0 ml of DMSO per liter of INO) to a co-culture media (like INO) may improve the health of explants, likely by controlling yeasts and fungi commonly found in and on seeds and can be a useful tool when performing large and/or automated tissue culture.

Moisture content of the seed at the time of excision may be varied, as well as the temperature of the seed at the time of excision. In addition, a storage parameter following excision may be varied. For instance, the relative humidity under which explant storage occurs may be varied. The explant storage temperature may also be varied, as well as the duration of explant storage, and the composition of the medium in which the explant is stored. Further parameters that may be manipulated include hydration and rehydration media compositions, incubation temperature, length of time, and transformation methods, among others.

Following excision, methods and apparatuses for screening transformable explant material from non-transformable damaged explants, cotyledons, seed coats, and other debris are employed as described in U.S. Patent Application Publication No. 2008/0280361. The methods may be performed manually, or may be partially or fully mechanized. For instance, one or more steps of sieving may be performed, using sieves of appropriate size based on size of the seeds being crushed and the explants being isolated. Bulk yield of crushed seed that has passed through the rollers may be put through a series of separation sieves, such that unwanted large and small debris are separated from the desired explant by size exclusion. This may be effectively accomplished, for instance with soybean material, using U.S. Standard sieves such as: #8 (2.36 mm opening), #10 (2.0 mm opening), #16 (1.18 mm opening), and others as appropriate (e.g. elongated window sieves such as 1/16"×3/4", 1/18"×3/4", 1/19"×1/2", or 1/20"×1/2"). Sieves with other opening sizes may be fabricated as needed for given seed sizes, based on the size of material being applied. The length of time for the screening process and the vigor of sieving may also be adjusted to enhance the throughput and/or yield of the process.

Other screening methods may also be utilized, such as by measuring differential buoyancy in solutions of explant material versus debris. A fraction of material that floats in an aqueous solution has been found to be enriched for intact transformable explants.

The explant may be recovered from a hydrated seed, from dry storable seed, from a partial rehydration of dried hydrated explant, wherein "hydration" and "rehydration" is defined as a measurable change in internal seed moisture percentage, or from a seed that is "primed"; that is, a seed that has initiated germination but has been appropriately placed in stasis pending favorable conditions to complete the germination process. Those of skill in the art will be able to use various hydration methods and optimize length of incubation time prior to transformation. The resulting explant is storable and can germinate and or be transformed when appropriate conditions are provided. Thus the new dry, storable meristem explant may be referred to as an artificial seed.

Following excision, one of skill in the art may store the explant according to the disclosed methods prior to subsequent use. Methods and parameters for drying, storing, and germinating seed are known in the art. Storage of excised explants comprising plant cells may be carried out using modifications of such storage conditions as desired, including temperatures, for example, of from about −80° C. to about 60° C. Temperatures of about −20° C. to room temperature in particular have been found to function well.

After isolated embryo explants comprising cells are contacted with the compositions of the present invention, the explants may be transformed by a selected heterologous DNA sequence, and transgenic plants may be regenerated therefrom. Transgenic plants may also be referred to as transgenic events. Various methods have been developed for transferring genes into plant tissue including high velocity microprojection, microinjection, electroporation, direct DNA uptake, and bacterially-mediated transformation. Methods of using various bacteria of species *Rhizobiaceae* as a vector for genetic transformation of plants and/or plant cells, and regenerating transgenic plants therefrom are known in the art. The host bacterial strain is often *Agrobacterium tumefaciens* ABI, C58, LBA4404, EHA101, or EHA105 carrying a plasmid having a transfer function for the expression unit. In certain non-limiting aspects of the present invention, *Agrobacterium*-mediated transformation and regeneration of a transgenic plant may be conducted as described in U.S. Pat. Nos. 5,824,877; 5,591,616; 5,981,840; and 6,384,301 Other bacterial strains also known to those skilled in the art of plant transformation are contemplated for use in the present invention, for example *Rhizobium*-mediated transformation as described in U.S. Patent Application Publication 2007/0271627, *Sinorhizobium* sp., *Mesorhizobium* sp., and *Bradyrhizobium* sp. (e.g. Broothaerts et al., 2005).

Means for preparing plasmids or vectors containing the desired genetic components are well known in the art. Generally, the heterologous DNA sequence is combined with one or more genetic components to prepare an expression unit. Often these expression units are provided with at least one T-DNA border for transfer of the sequence to the plant cells. One or more expression units are then inserted in a plasmid or vector which is then mobilized into bacteria which are then contacted with the cells. The bacteria transfer the expression unit to the cell and the expression unit get incorporated into the genome of the cell and then inherited from one generation to the other.

The genetic components are incorporated into a plasmid or vector molecule comprising at least one or more of the following genetic components: (a) a promoter that functions in plant cells to cause the production of an RNA sequence, (b) a structural DNA sequence that causes the production of an RNA sequence that encodes a product of commercial utility and/or a DNA sequence that causes the production of an RNAi molecule for inhibiting expression of a gene; and (c) a 3' non-translated DNA sequence that functions in plant cells to cause the addition of polyadenylated nucleotides to the 3' end of the RNA sequence.

Transcription of DNA into mRNA is regulated by a region of DNA usually referred to as the "promoter". The promoter region contains a sequence of bases that signals RNA polymerase to associate with the DNA and to initiate the transcription into mRNA using one of the DNA strands as a template to make a corresponding complementary strand of RNA. A number of promoters that are active in plant cells have been described in the literature. Such promoters would include but are not limited to the nopaline synthase (NOS) and octopine synthase (OCS) promoters that are carried on Ti plasmids of *Agrobacterium tumefaciens*, the caulimovirus promoters such as the cauliflower mosaic virus (CaMV) 19S and 35S promoters and the Figwort mosaic virus (FMV) 35S promoter, and the enhanced CaMV35S promoter (e35S). A variety of other plant gene promoters that are regulated in response to environmental, hormonal, chemical, and/or developmental signals, also can be used for expression of heterologous genes in plant cells, including, for instance, promoters regulated by (1) heat (Callis et al., 1988, (2) light (e.g., pea RbcS-3A promoter, Kuhlemeier et al., (1989);

maize RbcS promoter, Schaffner et al., (1991); (3) hormones, such as abscisic acid (Marcotte et al., 1989, (4) wounding (e.g., Wuni, Siebertz et al., 1989); or other signals or chemicals. Tissue specific expression is also known. As described below, it is preferred that the particular promoter selected should be capable of causing sufficient expression to result in the production of an effective amount of the gene product of interest. Examples describing such promoters include without limitation U.S. Pat. No. 6,437,217 (maize RS81 promoter), U.S. Pat. No. 5,641,876 (rice actin promoter), U.S. Pat. No. 6,426,446 (maize RS324 promoter), U.S. Pat. No. 6,429,362 (maize PR-1 promoter), U.S. Pat. No. 6,232,526 (maize A3 promoter), U.S. Pat. No. 6,177,611 (constitutive maize promoters), U.S. Pat. Nos. 5,322,938, 5,352,605, 5,359,142 and 5,530,196 (35S promoter), U.S. Pat. No. 6,433,252 (maize L3 oleosin promoter), U.S. Pat. No. 6,429,357 (rice actin 2 promoter as well as a rice actin 2 intron), U.S. Pat. No. 5,837,848 (root specific promoter), U.S. Pat. No. 6,294,714 (light inducible promoters), U.S. Pat. No. 6,140,078 (salt inducible promoters), U.S. Pat. No. 6,252,138 (pathogen inducible promoters), U.S. Pat. No. 6,175,060 (phosphorus deficiency inducible promoters), U.S. Pat. No. 6,635,806 (gamma-coixin promoter), and U.S. patent application Ser. No. 09/757,089 (maize chloroplast aldolase promoter). Additional promoters that may find use are a nopaline synthase (NOS) promoter (Ebert et al., 1987), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et al., 1987), the CaMV 35S promoter (Odell et al., 1985), the figwort mosaic virus 35S-promoter (Walker et al., 1987; U.S. Pat. Nos. 6,051,753; 5,378,619), the sucrose synthase promoter (Yang et al., 1990), the R gene complex promoter (Chandler et al., 1989), and the chlorophyll a/b binding protein gene promoter, PC1SV (U.S. Pat. No. 5,850,019), and AGRtu.nos (GenBank Accession V00087; Depicker et al, 1982; Bevan et al., 1983) promoters.

Promoter hybrids can also be constructed to enhance transcriptional activity (U.S. Pat. No. 5,106,739), or to combine desired transcriptional activity, inducibility and tissue specificity or developmental specificity. Promoters that function in plants include but are not limited to promoters that are inducible, viral, synthetic, constitutive as described, and temporally regulated, spatially regulated, and spatio-temporally regulated. Other promoters that are tissue-enhanced, tissue-specific, or developmentally regulated are also known in the art and envisioned to have utility in the practice of this invention.

The promoters used in the DNA constructs (i.e. chimeric/ recombinant plant genes) of the present invention may be modified, if desired, to affect their control characteristics. Promoters can be derived by means of ligation with operator regions, random or controlled mutagenesis, etc. Furthermore, the promoters may be altered to contain multiple "enhancer sequences" to assist in elevating gene expression.

The mRNA produced by a DNA construct of the present invention may also contain a 5' non-translated leader sequence. This sequence can be derived from the promoter selected to express the gene and can be specifically modified so as to increase or decrease translation of the mRNA. The 5' non-translated regions can also be obtained from viral RNAs, from suitable eukaryotic genes, or from a synthetic gene sequence. Such "enhancer" sequences may be desirable to increase or alter the translational efficiency of the resultant mRNA. The present invention is not limited to constructs wherein the non-translated region is derived from both the 5' non-translated sequence that accompanies the promoter sequence. Rather, the non-translated leader sequence can be derived from unrelated promoters or genes (see, for example U.S. Pat. No. 5,362,865). Examples of non-translation leader sequences include maize and petunia heat shock protein leaders (U.S. Pat. No. 5,362,865), plant virus coat protein leaders, plant rubisco leaders, GmHsp (U.S. Pat. No. 5,659,122), PhDnaK (U.S. Pat. No. 5,362, 865), AtAntl, TEV (Carrington and Freed, 1990), and AGR-tu.nos (GenBank Accession V00087; Bevan et al., 1983). Other genetic components that serve to enhance expression or affect transcription or translational of a gene are also envisioned as genetic components.

The 3' non-translated region of the chimeric constructs may contain a transcriptional terminator, or an element having equivalent function, and a polyadenylation signal that functions in plants to cause the addition of polyadenylated nucleotides to the 3' end of the RNA. The DNA sequences are referred to herein as transcription-termination regions. The regions are required for efficient polyadenylation of transcribed messenger RNA (mRNA). RNA polymerase transcribes a coding DNA sequence through a site where polyadenylation occurs. Examples of suitable 3' regions are (1) the 3' transcribed, non-translated regions containing the polyadenylation signal of *Agrobacterium* tumor-inducing (Ti) plasmid genes, such as the nopaline synthase (NOS; Fraley et al., 1983) gene, and (2) plant genes such as the soybean storage protein genes and the small subunit of the ribulose-1,5-bisphosphate carboxylase (ssRUBISCO) gene. An example of a preferred 3' region is that from the ssRUBISCO E9 gene from pea (European Patent Application 0385 962).

The present invention can be used with any suitable plant transformation plasmid or vector containing a scorable, selectable, or screenable marker and associated regulatory elements as described, along with one or more nucleic acids expressed in a manner sufficient to confer a particular desirable trait. Exemplary markers are known, and include but are not limited to GUS, green fluorescent protein (GFP), and luciferase (LUX), among others. Selectable or screenable markers function in regenerable plant tissue to produce a compound that confers upon the plant tissue resistance to an otherwise toxic compound. In certain embodiments, the vector comprises an aadA gene with associated regulatory elements encoding resistance to spectinomycin in plant cells. In a particular embodiment, the aadA gene comprises a chloroplast transit peptide (CTP) sequence that directs the transport of the aadA gene product to the chloroplast of a transformed plant cell. In other embodiments, the vector comprises a spectinomycin resistance gene with appropriate regulatory elements designed for expression in a bacterial cell, such as an *Agrobacterium* cell, so that the selection reagent may be added to a co-cultivation medium, and allowing obtention of transgenic plants for instance without further use of the selective agent after the co-culture period. Examples of suitable genes conferring traits of agronomic interest envisioned by the present invention would include but are not limited to genes for disease, insect, or pest tolerance, herbicide tolerance, genes for quality improvements such as yield, nutritional enhancements, environmental or stress tolerances, or any desirable changes in plant physiology, growth, development, morphology or plant product(s) including starch production (U.S. Pat. Nos. 6,538, 181; 6,538,179; 6,538,178; 5,750,876; 6,476,295), modified oils production (U.S. Pat. Nos. 6,444,876; 6,426,447; 6,380, 462), high oil production (U.S. Pat. Nos. 6,495,739; 5,608, 149; 6,483,008; 6,476,295), modified fatty acid content (U.S. Pat. Nos. 6,828,475; 6,822,141; 6,770,465; 6,706,950; 6,660,849; 6,596,538; 6,589,767; 6,537,750; 6,489,461; 6,459,018), high protein production (U.S. Pat. No. 6,380,466), fruit ripening (U.S. Pat. No. 5,512,466), enhanced animal and human nutrition (U.S. Pat. Nos. 6,723,837; 6,653,530; 6,5412,59; 5,985,605; 6,171,640), biopolymers (U.S. Pat. Nos. RE37,543; 6,228,623; 5,958,745 and U.S. Patent Publication No. US20030028917). Also environmental stress resistance (U.S. Pat. No. 6,072,103), pharmaceutical peptides and secretable peptides (U.S. Pat. Nos. 6,812,379; 6,774,283; 6,140,075; 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), fiber production (U.S. Pat. Nos. 6,576,818; 6,271,443; 5,981,834; 5,869,720) and biofuel production (U.S. Pat. No. 5,998,700). Any of these or other genetic elements, methods, and transgenes may be used with the invention as will be appreciated by those of skill in the art in view of the instant disclosure.

Alternatively, the DNA sequences of interest can affect these phenotypes by encoding a an RNA molecule that causes the targeted inhibition of expression of an endogenous gene via gene silencing technologies such as antisense-, co-suppression-mediated mechanisms, RNAi technologies including miRNA (e.g., U.S. Patent Application Publication 2006/0200878).

Exemplary nucleic acids that may be introduced by the methods encompassed by the present invention include, for example, DNA sequences or genes from another species, or even genes or sequences that originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes that are normally present yet that one desires, e.g., to have over-expressed. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA that is already present in the plant cell, DNA from another plant, DNA from a different organism, or a DNA generated externally, such as a DNA sequence containing an antisense message of a gene, or a DNA sequence encoding a synthetic or modified version of a gene.

The T-DNAs may be bound by RB and/or LB sequences or may have no border sequences. The sequences that may be transferred into a plant cell may be present on one transformation vector in a bacterial strain being utilized for transformation. In another embodiment, the sequences may be present on separate transformation vectors in the bacterial strain. In yet another embodiment, the sequences may be found in separate bacterial cells or strains used together for transformation.

The DNA constructs used for transformation in the methods of present invention may also contain the plasmid backbone DNA segments that provide replication function and antibiotic selection in bacterial cells, for example, an *Escherichia coli* origin of replication such as ori322, a broad host range origin of replication such as oriV or oriRi, and a coding region for a selectable marker such as Spec/Strp that encodes for aminoglycoside adenyltransferase (aadA) conferring resistance to spectinomycin or streptomycin (e.g. U.S. Pat. No. 5,217,902. In light of this disclosure, numerous other possible regulatory elements, and other sequences of interest will be apparent to those of skill in the art. Therefore, the foregoing discussion is intended to be exemplary rather than exhaustive.

Those of skill in the art are aware of the typical steps in the plant *Agrobacterium*-mediated transformation process. The *Agrobacterium* can be prepared either by inoculating a liquid such as Luria Burtani (LB) media directly from a glycerol stock or streaking the *Agrobacterium* onto a solidified media from a glycerol stock, allowing the bacteria to grow under the appropriate selective conditions, generally from about 26° C.-30° C., or about 28° C., and taking a single colony or a small loop of *Agrobacterium* from the plate and inoculating a liquid culture medium containing the selective agents. Those of skill in the art are familiar with procedures for growth and suitable culture conditions for *Agrobacterium* as well as subsequent inoculation procedures. The density of the *Agrobacterium* culture used for inoculation and the ratio of *Agrobacterium* cells to explant can vary from one system to the next, and therefore optimization of these parameters for any transformation method is expected.

Typically, an *Agrobacterium* culture is inoculated from a streaked plate or glycerol stock and is grown overnight and the bacterial cells are washed and resuspended in a culture medium suitable for inoculation of the explant. Suitable inoculation media for the present invention include, but are not limited to ½ MS PL or ½ MS VI for immature embryo explants (see Tables 1 and 2, respectively, and INO (see Table 6) for mature embryo explants.

The next stage of the *Agrobacterium* mediated transformation process is the inoculation. In this stage the explants and *Agrobacterium* cell suspensions are mixed together. In embodiments of the present invention where the embryo explants are of immature corn embryos, embryo explants are placed directly into the inoculation medium containing the *Agrobacterium*. Embryos are cultured in inoculation media for less than 30 min. The inoculation is generally performed at a temperature of about 15° C. to 30° C., or about 23° C. to 28° C. The inoculation can also be done by isolating the immature embryos directly onto the co-culture medium (described below) and then spotting 1 μL of *Agrobacterium* solution onto the embryo or alternatively placing a piece of filter paper saturated in *Agrobacterium* solution over the top of the embryos for about 5 to 60 minutes. The filter paper and any excess solution are then removed before co-culture.

In certain embodiments, at the time, or subsequent to the time that a heterologous DNA is contacting the explant, the explant may be contacted by one or more plant growth regulators (PGRs). Many PGRs are known in the art and are contemplated in such embodiments, such as auxins, antiauxins, cytokinins, gibberellins, herbicides, growth inhibitors and retardants, morphactins, growth stimulators and/or other unclassified plant growth regulators, as listed elsewhere in the present disclosure.

After inoculation, any excess *Agrobacterium* suspension can be removed and the *Agrobacterium* and target plant material are co-cultured. The co-culture refers to the time post-inoculation and prior to transfer to a delay or selection medium. Any number of plant tissue culture media can be used for the co-culture step. In certain embodiments, after inoculation with *Agrobacterium* the plant tissues are cultured on a semi-solid MS-based, or reduced salt ½ MS-based semi-solid co-culture medium with a gelling agent such as agarose, or a low EEO agarose (Table 3).

TABLE 3

MS Based semi-solid co-culture medium.

| Ingredient | Source | ½ MS Based co-culture medium Amount per liter | MS Based co-culture medium Amount per liter |
|---|---|---|---|
| MS Basal Salts | Phytotech M524 | 2.165 g | 4.33 g |
| MS Vitamins | Phytotech M533 | 103.1 mg | 103.1 mg |
| Thiamine HCL | Sigma T-3902 | 0.5 mg | 0.5 mg |
| 2,4-D | Phytotech D295 | 3 mg | 0.5 mg |
| Glucose | Phytotech G386 | 10 g | 0 |
| Sucrose | Phytotech S391 | 20 g | 30 g |
| Proline | Sigma P-5607 | 0.115 g | 1.38 g |
| Casamino Acids | Difco DF0288-17 | 0 | 0.5 g |
| Agarose, Low EEO | Sigma A-6013 | 5.5 g | 5.5 g |
| Acetosyringone | Aldrich, D134406 | 40 mg | 40 mg |
| Silver Nitrate | Sigma S-6506 | 3.4 mg | 3.4 mg |
| Carbenicillin | Phytotech C346 | 0 | 50 mg |
| pH | | 5.2 | 5.8 |

The co-culture is typically performed for about one to three days or for less than 24 hours at a temperature of about 18° C. to 30° C., or about 20° C. to 25° C. The co-culture can be performed in the light or in light-limiting conditions. Usually, the co-culture is performed in light-limiting conditions. "Light-limiting conditions" as used herein are defined as any conditions that limit light during the co-culture period including but not limited to covering a culture dish containing the plant and *Agrobacterium* mixture with a cloth, foil, or placing the culture dishes in a black bag, or placing the cultured cells in a dark room. Lighting conditions can be optimized for each plant system as is known to those of skill in the art.

In embodiments of the present invention where the embryo explants are of mature soy embryos, embryo explants are exposed to the prepared inoculum, and briefly exposed to sonication energy from a standard laboratory water bath cleaning sonicator such as L&R Ultrasonics QS140 (L&R Manufacturing Co., Kearny, N.J.); or a Honda W113 sonicator (Honda, Denshi Japan) for 20 seconds. After the brief sonication step, explants are drained of originating inoculum and transferred to fresh PLANTCONs each containing filter paper moistened with INO media, usually within several hours after commencement of transfection. Explants are then incubated in a lighted chamber (generally 16 hours of light at ≥5 uE) at approximately 23 to 28 C for 1 to 5 days. Co-culture and subsequent steps may be performed in dark conditions, or in the light, e.g. lighted Percival incubators, for instance for 2 to 5 days (e.g. a photoperiod of 16 hours of light/8 hours of dark, with light intensity of ≥5 µE, such as about 5-200 µE or other lighting conditions that allow for normal plastid development) at a temperature of approximately 23 to 25° C., and may be performed at up to about 35° C. or 40° C.

After co-culture with *Agrobacterium* or after bombardment with the microprojectile, the explants can be placed directly onto regeneration media, typically containing a selective agent. Explants (regardless of transformation method) are placed on selective media for from about 7 to about 42 days, or from about 7 to about 30 days, or from about 7 to about 21 days, or from about 7 to about 14 days. A variety of tissue culture media and transfer requirements are known that can be implemented and optimized to support plant tissue growth and development for plant transformation and recovery of transgenic plants. These tissue culture media can either be purchased as a commercial preparation or custom prepared and modified by those of skill in the art. Examples of such media include, but are not limited to those described by Murashige and Skoog, (1962); Chu et al., (1975); Linsmaier and Skoog, (1965); Uchimiya and Murashige, (1962); Gamborg et al., (1968); Duncan et al., (1985); McCown and Lloyd, (1981); Nitsch and Nitsch (1969); and Schenk and Hildebrandt, (1972), or derivations of these media supplemented accordingly. Those of skill in the art are aware that media and media supplements such as nutrients and growth regulators for use in transformation and regeneration are usually optimizable for a particular target crop or variety of interest. Tissue culture media may be supplemented with carbohydrates such as, but not limited to, glucose, sucrose, maltose, mannose, fructose, lactose, galactose, and/or dextrose, or ratios of carbohydrates. Reagents are commercially available and can be purchased from a number of suppliers (see, for example Sigma Chemical Co., St. Louis, Mo.; and PhytoTechnology Laboratories, Shawnee Mission, Kans.). Additional appropriate media components can be added to the selection or delay medium to inhibit *Agrobacterium* growth. Such media components can include, but are not limited to, antibiotics such as carbenicillin or cefotaxime. The cultures are subsequently transferred to a media suitable for the recovery of transformed plantlets. Those of skill in the art are also aware of the numerous modifications in selective regimes, media, and growth conditions that can be varied depending on the plant system and the selective agent. Typical selective agents include but are not limited to antibiotics such as geneticin (G418), kanamycin, paromomycin, spectinomycin, or other chemicals such as glyphosate or other herbicides. In a specific embodiment of the present invention, the selective agent is spectinomycin. Spectinomycin resistant shoots that have green buds or leaves are screenable or scoreable as being spectinomycin resistant. They may be placed in soil or on a soil substitute such as on a rooting medium, in the presence or absence of the selective agent. Shoots elongating from such an explant are routinely shown to be transgenic and give rise to $R_1$ and subsequent progeny that are transgenic, while the roots developing from such explants may be transgenic or non-transgenic. Thus, a plant comprising a transgenic shoot and a partly or fully non-transgenic root system is also contemplated. Alternatively, a method for regenerating a whole plant from transgenic shoots from transformed meristematic tissue while roots are non-transgenic, by culturing of transformed tissue on a medium lacking a selective agent, is also contemplated, such as disclosed in U.S. Patent Application Publication No. 2008/0057512.

These methods can also be done in one or more containers and the process may be manual, or automated using state of the art automation. Media and culture conditions disclosed in the present invention can be modified or substituted with nutritionally equivalent components, or similar processes for selection and recovery of transgenic events, and still fall within the scope of the present invention. A transgenic plant formed using *Agrobacterium* transformation methods typically (although not always) contains a single simple recombinant DNA sequence (single copy) inserted into one chromosome and is referred to as a transgenic event. Such transgenic plants can be referred to as being heterozygous for the inserted exogenous sequence. A transgenic plant homozygous with respect to a transgene can be obtained by sexually mating (selfing) an independent segregant transgenic plant that contains a single exogenous gene sequence to itself, for example an $R_0$ plant, to produce $R_1$ seed. One fourth of the $R_1$ seed produced will be homozygous with respect to the transgene. Germinating $R_1$ seed results in plants that can be tested for zygosity, typically using a SNP assay or a thermal amplification assay that allows for the distinction between heterozygotes and homozygotes (i.e., a zygosity assay).

To confirm the presence of the exogenous DNA or "transgene(s)" in the transgenic plants a variety of assays may be performed. Such assays include, for example, "molecular biological" assays, such as Southern and northern blotting and PCR™, INVADER assays, Recombinase Polymerase Amplification (RPA) method (see for example U.S. Pat. No. 7,485,428); "biochemical" assays, such as detecting the presence of a protein product, e.g., by immunological means (ELISAs and western blots) or by enzymatic function; plant part assays, such as leaf or root assays; and also, by analyzing the phenotype of the whole regenerated plant.

Once a transgene has been introduced into a plant, that gene can be introduced into any plant sexually compatible with the first plant by crossing, without the need for ever directly transforming the second plant. Therefore, as used herein the term "progeny" denotes the offspring of any generation of a parent plant prepared in accordance with the instant invention, wherein the progeny comprises a selected DNA construct. A "transgenic plant" may thus be of any generation. "Crossing" a plant to provide a plant line having one or more added transgenes or alleles relative to a starting plant line is defined as the techniques that result in a particular sequence being introduced into a plant line by crossing a starting line with a donor plant line that comprises a transgene or allele. To achieve this one could, for example, perform the following steps: (a) plant seeds of the first (starting line) and second (donor plant line that comprises a desired transgene or allele) parent plants; (b) grow the seeds of the first and second parent plants into plants that bear flowers; (c) pollinate a flower from the first parent plant with pollen from the second parent plant; and (d) harvest seeds produced on the parent plant bearing the fertilized flower.

Another aspect of the present invention is a transgenic plant and any plant parts thereof as defined elsewhere in the present disclosure, created using the methods of the present invention disclosed herein.

EXAMPLES

Those of skill in the art will appreciate the many advantages of the methods and compositions provided by the present invention. The following examples are included to demonstrate certain embodiments of the invention. Those of skill in the art should, in light of the present disclosure, appreciate that many changes can be made in the specific embodiments that are disclosed and still obtain a like or similar result without departing from the spirit and scope of the invention. All references cited herein are incorporated herein by reference to the extent that they supplement, explain, provide a background for, or teach methodology, techniques, or compositions employed herein.

Example 1

Enhanced Transformation of Soybean Cells Contacted with PEG in Water

This example demonstrates enhanced transformation of dry soybean embryos that were contacted with a composition containing PEG in sterile distilled water (SDW). Soybean cv. A3525 dry embryos were excised according to the method described in U.S. Patent Application Publication No. 2008/0280361 and contacted for an hour with various amounts of 5, 10, 20, or 50% PEG-4000 dissolved in SDW. The embryos were rinsed 5-6× with SDW and transformed according to the methods described in U.S. Patent Application Publication No. 2009/0138985. The embryos were transformed with a 2T transformation vector having an OriRi or OriV replication of origin and contained in ABI or AB30 strain of *Agrobacterium*. The embryos were regenerated on spectinomycin selection medium. As shown in Table 4, embryos contacted with 5, 10, and 20% PEG composition generally showed enhanced transformation frequency, and enhanced frequency of single copy events, compared to embryos contacted with INO medium or SDW alone. Embryos that were contacted with 50% PEG also demonstrated an improved TF (7%) as compared to embryos that were contacted with SDW (TF=2.3%). The 50% PEG experiment was done with an AB30/OriRi construct. See Table 5 for spectinomycin selection medium composition for soybean.

TABLE 4

Transformation frequency of soybean cells contacted with PEG in water compared to water or INO medium.

| Treatment | TF % (ABI/OriRi) | TF % (AB30/OriV) |
|---|---|---|
| INO medium | 5.9 | 6.2 |
| H2O | 2.3 | 1.7 |
| 1% PEG in H2O | 1.9 | 3.7 |
| 5% PEG in H2O | 8.1 | 5.2 |
| 10% PEG in H2O | 14.3 | 12.3 |
| 20% PEG in H2O | 19.6 | 12.2 |

TABLE 5

Spectinomycin selection medium composition for soybean.

| Ingredient | Source | Amount per liter |
|---|---|---|
| LM Woody Plant Medium w/Vitamins | Phytotech L449 | 2.41 g |
| Sucrose | Phytotech S391 | 20 g |
| Calcium Gluconate | Sigma G-4625 | 1.29 g |
| Agargel | Sigma A-3301 | 4 g |
| Carbenicillin (40 mg/mL stock) | Phytotech C346 | 5 mL |
| Timentin (100 mg/mL stock) | Duchefa T0190 | 1 mL |
| Cefotaxime (50 mg/mL stock) | Midwest NDC0039-0019-10 | 4 mL |
| Spectinomycin (50 mg/mL stock) | Sigma S-4014 | 3 mL |

Example 2

Enhanced Transformation of Soybean Cells Contacted with PEG in INO Medium

This example demonstrates enhanced transformation of dry soybean embryos that were contacted with a composition containing PEG in INO or INO medium. Soybean cv. A3525 dry embryos were excised according to the method described in U.S. Patent Application Publication No. 2008/0280361 and contacted for an hour with 20% PEG-4000 dissolved in INO. The embryos were rinsed 5-6× with plain INO and transformed according to the methods described in U.S. Patent Application Publication No. 2009/0138985. The embryos were transformed with a 2T transformation vector having an OriRi replication of origin and contained in AB30 strain of *Agrobacterium*. The embryos were regenerated on spectinomycin selection medium. As shown in Table 6, embryos contacted with 20% PEG composition generally showed enhanced transformation frequency compared to embryos contacted with INO medium alone in two different experiments. See Table 7 for INO medium composition.

TABLE 6

Transformation frequency of soybean cells contacted with PEG in INO compared to INO.

| Treatment | # Explants | # Events to Soil | TF % |
|---|---|---|---|
| INO | 4135 | 210 | 5.1 |
| 20% PEG in INO | 4049 | 317 | 7.8 |
| INO | 4149 | 163 | 3.9 |
| 20% PEG in INO | 4110 | 341 | 8.3 |

TABLE 7

Composition of inoculation medium (INO)

| Ingredient | Amount per liter |
|---|---|
| Magnesium sulfate (Fisher M63) | 0.1 g |
| Ammonium sulfate (Fisher A702) | 53.6 mg |
| Sodium phosphate monohydrate (Fisher S369-500) | 60 mg |
| Calcium chloride (Sigma C-3881) | 60 mg |
| Boric acid (Fisher A73-3) | 0.3 mg |
| Manganese sulfate (Sigma I-2550) | 1 mg |
| Zinc sulfate heptahydrate (Sigma Z-1001) | 0.2 mg |
| Potassium iodide (Sigma P-8166) | 0.075 mg |
| Sodium Molybdate dihydrate (Sigma S-6646) | 0.025 mg |
| Cupric sulfate (Fisher C493-500) | 2.5 µg |
| Cobalt chloride hexahydrate (Sigma C-2911) | 2.5 µg |
| Sequestrene (Ciba 964603) | 2.8 mg |
| Potassium nitrate (Sigma P-8291) | 1 g |
| Glucose (Phytotech G386) | 30 g |
| MES (Sigma M8250) | 3.9 g |
| Bring volume to 1 L with de-ionized distilled water | |
| pH with KOH to | 5.4 |
| Autoclave | |
| Add sterile vitamin stock containing the following | |
| Myo-inositol (Sigma I-3011) | 10 mg |
| Nicotinic acid (Sigma N-0765) | 0.1 mg |
| Pyridoxine HCl (Sigma P-8666) | 0.1 mg |
| Thiamine HCl (Sigma T-3902) | 1 mg |

Example 3

Enhanced Transformation of Soybean Cells Contacted with PEG in BGM

This example demonstrates enhanced transformation of dry soybean embryos that were contacted with a composition containing PEG in Bean Germination Medium (BGM—Table 8) compared to BGM alone. Soybean cv. A3525 dry embryos were excised according to the method described in U.S. Patent Application Publication No. 2008/0280361 and contacted for an hour with 10% or 20% PEG-4000 dissolved in BGM. The embryos were rinsed 5-6× with BGM and transformed according to the methods described in U.S. Patent Application Publication No. 2009/0138985. The embryos were transformed with a 2T transformation vector having an OriV replication of origin and contained in AB30 strain of *Agrobacterium*. The embryos were regenerated on spectinomycin selection medium. As shown in Table 9, embryos contacted with 10% and 20% PEG composition showed enhanced transformation frequency compared to embryos contacted with BGM alone.

TABLE 8

Composition of Bean Germination Medium (BGM).

| Ingredient | Source | Amount per liter |
|---|---|---|
| $NH_4NO_3$ | (Sigma A-3795) | 240 mg |
| $KNO_3$ | (Sigma P-8291) | 505 mg |
| $CaCl_2 \cdot 2H_2O$ | (Sigma C3881) | 176 mg |
| $MgSO_4 \cdot 7H_2O$ | (Fisher M63) | 493 mg |
| $KH_2PO_4$ | (Fisher BP362-500) | 27 mg |
| $H_3BO_3$ | (Fisher BP168-1) | 1.86 mg |
| $Na_2MoO_4 \cdot 2H_2O$ | (Sigma S-6646) | 0.216 mg |
| $MnSO_4 \cdot H_2O$ | (Sigma I-2550) | 5.07 mg |
| $ZnSO_4 \cdot 7H_2O$ | (Sigma Z1001) | 2.58 mg |
| $FeSO_4 \cdot 7H_2O$ | (Sigma F8263) | 2.502 mg |
| KI | (Sigma P-8256) | 0.249 mg |
| $Na_2EDTA \cdot 2H_2O$ | (Fisher BP120) | 3.348 mg |
| $CuSO_4 \cdot 5H_2O$ | (Sigma C-3036) | 0.0008 mg |
| $CoCl_2 \cdot 6H_2O$ | Sigma C-2911) | 0.0008 mg |
| Thiamine HCl | Sigma C-2911) | 1.34 mg |
| Nicotinic Acid | (Sigma N-0765) | 0.5 mg |
| Pyridoxine HCl | (Sigma P-8666) | 0.82 mg |
| Bravo (75% WP) | (Carlin) | 30 mg |
| Captan (50% WP) | (Carlin 10-0250) | 30 mg |
| Sucrose | (Phytotech S391) | 25000 mg |
| pH | | 5.8 |

TABLE 9

Transformation frequency of soybean cells contacted with PEG in BGM compared to BGM medium.

| Treatment | Explants | # R0 Plants | TF |
|---|---|---|---|
| BGM | 1635 | 12 | 0.73% |
| BGM 10% PEG | 1562 | 39 | 2.50% |
| BGM 20% PEG | 1487 | 38 | 2.56% |

Example 4

Effect of PEG on TF Compared to Other Osmotic Compounds

This example demonstrates the effect of other osmotic compounds on TF compared to PEG. It also compares TF enhancement of treatments with various PEG species. Soybean cv. A3555 dry embryos were excised according to the method described in U.S. Patent Application Publication No. 2008/0280361 and contacted for an hour with various amounts of PEG-4000, PEG-6000, PEG-8000, Mannitol, Sorbitol, or Glycerol dissolved in SDW. The embryos were then rinsed 5-6× with SDW and transformed according to the methods described in U.S. Patent Application Publication No. 2009/0138985. The embryos were transformed with a 2T transformation vector having an OriRi replication of origin and contained in AB30 strain of *Agrobacterium*. The embryos were regenerated on spectinomycin selection medium. As shown in Table 10, embryos contacted with 10% and 20% PEG compositions showed enhanced transformation frequency compared to embryos treated with other osmotic compounds, or with water alone.

TABLE 10

Transformation frequency soybean cells contacted with PEG compared to other osmotic compounds.

| Treatment | Initial Explants | # R0 Plants | TF |
|---|---|---|---|
| H2O | 1562 | 76 | 4.90% |
| 20% PEG4000 | 1165 | 177 | 15.20% |
| 10% PEG6000 | 1088 | 99 | 9.10% |
| 20% PEG6000 | 1280 | 220 | 17.20% |
| 10% PEG8000 | 1485 | 113 | 7.60% |
| 20% PEG8000 | 1478 | 215 | 14.50% |
| 10% mannitol | 1008 | 5 | 0.50% |
| 10% sorbitol | 1034 | 4 | 0.40% |
| 20% sorbitol | 906 | 3 | 0.30% |
| 10% glycerol | 174 | 4 | 2.30% |
| 20% glycerol | 205 | 0 | 0.00% |

Example 5

PEG Regulates the Rate of Hydration in Dry Embryo Explants

This example demonstrates that PEG is useful for regulating the rate of hydration of dry embryo explants. Soybean cv. A3525 dry embryos were excised according to the method described in U.S. Patent Application Publication No. 2008/0280361. The explants were then contacted with either 20% PEG4000 dissolved in INO, or INO alone. The rate of moisture intake was measured by taking samples of the explants at timed intervals during treatment and then subjecting them to a destructive gravimetric-based oven test in which explants were dried in a ~100° C. oven for approximately two days. Percent moisture was determined from their weight loss. A first study examined hydration rates at 1, 4, and 24 hours, while a second study examined rate of hydration rates at 0, 15, 30, 45, and 60 minutes, as shown in tables 11 and 12, respectively. Both studies indicate the rate of moisture intake by dry soy embryos explants that are contacted with 20% PEG4000 is reduced. Regulating hydration with

TABLE 11

Hydration of dry embryo explants contacted with PEG compared to INO medium recorded in hourly intervals.

| | Moisture Content | |
|---|---|---|
| Time (hours) | INO | 20% PEG4000 in INO |
| 0 | 5.8% +/− 0.1% | 5.8% +/− 0.1% |
| 1 | 64.4% +/− 0.3% | 55.2% +/− 0.2% |
| 4 | 63.6% +/− 0.4% | 58.7% +/− 0.3% |
| 24 | 64.6% | 57.7% |

TABLE 12

Hydration of dry embryo explants contacted with PEG compared to INO medium recorded in 15 minute intervals.

| | Moisture Content | |
|---|---|---|
| Time (minutes) | INO | 20% PEG4000 in INO |
| 0 | 5.8% +/− 0.1% | 5.8% +/− 0.1% |
| 15 | 51.2% +/− 0.5% | 44.6% +/− 0.5% |
| 30 | 59.6% +/− 0.6% | 52.1% +/− 0.4% |

TABLE 12-continued

Hydration of dry embryo explants contacted with PEG compared to INO medium recorded in 15 minute intervals.

| | Moisture Content | |
|---|---|---|
| Time (minutes) | INO | 20% PEG4000 in INO |
| 45 | 60.7% +/− 2.0% | 54.5% +/− 0.9% |
| 60 | 63.20% | 58.10% |

Example 6

PEG-Treatment Reduces Exudates Release of Embryo Explants

This example demonstrates that dry-excised embryo explants contacted with PEG in water release less exudates compared to those contacted with water alone. Soybean cv. A3555 dry embryos were excised according to the method described in U.S. Patent Application Publication No. 2008/0280361 and contacted for an hour with 20% PEG-4000 in SDW, or SDW alone. The explants, in their respective media were placed on an orbital shaker, at 75 RPM and incubated at room temperature. Samples of the media from each group were taken after 0, 15, 30, 45, and 60 minutes of incubation, and analyzed for exudates as measured by optical density (absorbance at 300 nm, blanked with appropriate medium) and conductivity (in microsiemens). As shown in Table 13, optical density of exudates was much higher in water control samples compared to samples from the 20% PEG treatment. The same was true of conductivity. Note: Readings denoted with an asterisk (*) were done with 1/10 dilutions of samples and then multiplied by 10 because spectrophotometer used had a maximum range of 3.295.

TABLE 13

Optical density and conductivity of explants treated with PEG compared water treatment.

| | Optical Density (A300 nm) | | Conductivity (µS) | |
|---|---|---|---|---|
| Time (minutes) | H20 | 20% PEG-4000 | H20 | 20% PEG-4000 |
| Media Blank | 0 | 0 | 2.6 | 124 |
| 0 | 0.512 | 0.203 | 68.5 | 148.5 |
| 15 | 3.74* | 1.132 | 748.6 | 336.2 |
| 30 | 6.25* | 1.756 | 1011 | 447.8 |
| 45 | 7.06* | 2.411 | 1152 | 519.8 |
| 60 | 7.46* | 2.849 | 1320 | 557.4 |

Example 7

Effect of PEG Treatment on Transformation Frequency of Hydrated Soybean Embryos

This example demonstrates the effect of PEG treatment on transformation frequency of hydrated soybean embryos when contacted prior to *Agrobacterium*-mediated transformation. Soybean cv. A3525 soybean embryos were excised according to the method described in U.S. Patent Application Publication No. 2008/0280361 and contacted for an hour with various amounts of PEG-4000 in SDW. The embryos were rinsed 5-6× with SDW and transformed according to the methods described in U.S. Pat. No. 7,402,734. The embryos were transformed with a 2T transformation vector having an OriRi replication of origin and contained in AB30 strain of *Agrobacterium*. The embryos were regenerated on spectinomycin selection medium. As shown in Table 14, PEG treatment did not appear to be useful in enhancing TF of already hydrated soybean mature embryos. It may be that PEG treatment is beneficial to dry embryos, and immature embryos as exemplified with the corn immature embryos below.

TABLE 14

Transformation frequency of hydrated soybean cells contacted with PEG in water compared to water.

| Treatment | Explants | # Rooted | TF |
|---|---|---|---|
| H2O | 394 | 66 | 16.75% |
| 1% PEG | 436 | 43 | 9.86% |
| 5% PEG | 393 | 45 | 11.45% |
| 10% PEG | 374 | 42 | 11.23% |
| 20% PEG | 387 | 25 | 6.46% |

Example 8

Effect of Use of PEG During Co-Culture on Transformation Frequency

This example demonstrates the effect of PEG composition during co-culture on transformation frequency. Soybean cv. A3555 dry embryos were excised according to the method described in U.S. Patent Application Publication No. 2008/0280361 and contacted for an hour with 20% PEG-4000 dissolved in SDW. The embryos were rinsed 5-6× with SDW and transformed according to the methods described in U.S. Patent Application Publication No. 2009/0138985. The embryos were transformed with a 2T transformation vector having an OriRi replication of origin and contained in AB30 strain of *Agrobacterium*. The transformed cells were then co-cultured in INO medium containing 1, 5, 10, or 20% PEG 4000. Co-culture medium also contained 1 ppm TDZ. The embryos were regenerated on spectinomycin selection medium. As shown in Table 15, treatments in which PEG was included in co-culture medium yielded a lower TF compared to treatments in which PEG was used prior to co-culture. This suggests that while PEG treatment prior to transformation improves competency of cells for bacterially-mediated transformation, PEG during co-culture appears to reduce TF.

TABLE 15

Transformation frequency of soybean cells contacted with PEG during co-culture.

| Treatment | Co-culture Medium | Initial Explants | # R0 Plants | TF |
|---|---|---|---|---|
| H2O | INO | 1562 | 76 | 4.90% |
| 20% PEG4000 | INO | 1165 | 177 | 15.20% |
| 20% PEG4000 | 1% PEG4000 in INO | 922 | 84 | 9.10% |
| 20% PEG4000 | 5% PEG4000 in INO | 782 | 52 | 6.60% |
| 20% PEG4000 | 10% PEG4000 in INO | 922 | 17 | 1.80% |
| 20% PEG4000 | 20% PEG4000 in INO | 762 | 0 | 0.00% |

Example 9

Enhanced Callus Production of Corn Embryos Contacted with PEG

This example demonstrates that PEG and different amounts (%) of PEG can be used for improving callus production. Corn embryos from corn ears were isolated manually as described elsewhere in the present disclosure and pooled. The embryos were stored in either 1 ml of Lynx 2304, or 1 ml of Lynx 2304 medium containing different amounts of PEG 8000 (Sigma P-2139) at 6° C. for 4 days in dark. Four replicates of each treatment were performed. The embryos were subsequently cultured on callus induction medium Lynx 1074 for about 2 weeks. See Table 17 for Lynx 1074 and 2304 media compositions. As shown in Table 16, in the control treatment (no storage), 100% of the embryos produced callus when they were cultured directly on Lynx 2304 medium after isolation. A small percentage of embryos produced callus when they were stored in 1% or 5% of PEG8000. None of the embryos produced callus when they were stored in a medium without PEG (trt 2). 100% of the embryos stored in 10 or 20% of PEG 8000 produced callus (trts 5 & 6).

TABLE 16

Effect of PEG on callus response in corn immature embryos.

| Treatment | % PEG (V/V) | Culture response and comments |
|---|---|---|
| 1 | Control (no storage, cultured immediately after isolation) | 100% of the embryos produced embryogenic callus response |
| 2 | 0 | Embryos didn't produce embryogenic culture response, died during culture |
| 3 | 1 | 10% embryos produced embryogenic culture response |
| 4 | 5 | 20% embryos produced embryogenic culture response |
| 5 | 10 | 100% embryos produced embryogenic culture response |
| 6 | 20 | |

TABLE 17

Media compositions used in the invention.

| Media Components/L (Suppliers) | Lynx1074 | Lynx2304* |
|---|---|---|
| MS Basal Salts (Phytotech M524) | 4-33 g | 4.33 g |
| MS Vitamins (100X) (Phytotech M533) | 10 mL | 10 mL |
| Thiamine HCL (Sigma T-3902) | 0.5 mg | 0.5 mg |
| 2,4-D (Phytotech D295) | 0.5 mg | 0 |
| Sucrose (Phytotech S391) | 30 g | 30 g |
| Proline (Sigma P-5607) | 1-38 g | 1.38 g |
| Casamino Acids (Difco DF0288-17) | 0-5 g | 0.5 g |
| pH | 5.8 | |
| Low EEO Agarose (Sigma A-6013) | 0 | 0 |
| Phytagel (Sigma P-8169) | 3.0 g | 0 |
| Picloram (Sigma P-5575) | 2.2 mg | 0 |
| Carbenicillin (Phytotech C346) | 0 | 0 |
| Acetosyringone (Aldrich, D134406) | 0 | 0 |
| BAP (Sigma B-3408) | 0 | 0 |
| Silver Nitrate (Sigma S-6506) | 3.4 mg | 0 |

*Volume was adjusted to 800 ml and medium is stored after filter sterilization (FS) without pH adjustment. Prior to use, PEG and all other additives in described in Examples were added and volume/pH was adjusted prior to FS.

Example 10

This example demonstrates the use of PEG of different molecular weights for improving competency of plant cells. Corn embryos from corn ears were isolated manually as described elsewhere in the present disclosure and pooled, then stored in either 1 ml of Lynx 2304, or 1 ml of Lynx 2304 medium containing 20% PEG of different molecular weight for 4 days at 6° C. in dark. They were subsequently cultured on Lynx 1074 for 2 weeks to observe callus response. As shown in Table 18, In the control treatment (no storage), 100% of the embryos produced callus when they were cultured directly on Lynx 2304 medium after isolation. No callus was formed by embryos that were not stored in the absence of PEG, while generally all embryos produced callus when contacted with PEG. Furthermore, the callus formation increased as the molecular weight of PEG increased from 200 to 8000.

TABLE 18

Effect of various PEG species on callus response in corn immature embryos.

| Treatment | SigmaCat# | Ave Mol. Wt | m osm/l | Culture response and comments |
|---|---|---|---|---|
| A0 | Control (No storage) | | N/A | 100% embryos produced embryogenic callus |
| A1 | No PEG | | 171 | Embryos didn't produce embryogenic culture response, died during culture |
| A2 | P-3015 | 200 | 1608 | 30% embryos produced embryogenic culture response |
| A3 | P-3265 | 400 | 1116 | 50% embryos produced embryogenic culture response |
| A4 | P-3515 | 950-1050 | 742 | 80% embryos produced culture response; good embryogenic callus |
| A5 | P-5402 | 1450 | 626 | Excellent embryogenic callus formation. |
| A6 | P-4338 | 3350 | 586 | Treatments were undistinguishable from each other |
| A7 | P-2139 | 8000 | 532 | |

Example 11

This example illustrates improvement in transformation frequency of corn embryos contacted with PEG prior to transformation. Corn immature embryos were isolated manually as described elsewhere in the present disclosure from inbred line LH 244 and divided into treatments. Embryos from one treatment were contacted with medium Lynx 2304 containing 20% W/V PEG8000 for 10 min., then washed three times with sterile ddH$_2$O. Another treatment received no PEG treatment following embryo isolation. Both treatments were inoculated with *Agrobacterium* (OD 0.1 at 660 nm) for 5 minutes and subsequently cultured for selection and regeneration as described in U.S. Pat. No. 7,682,829.

As shown in Table 19, the embryos that were contacted with PEG produced higher number of transgenic sectors and eventually higher number of transgenic plants, indicating that contacting corn embryos with PEG improves their transformation competency.

TABLE 19

Transformation frequency of corn embryos treated with PEG.

| Treatment | # Embryos to selection medium | GFP positive Sectors | # transgenic plants produced | % TF |
|---|---|---|---|---|
| No PEG Treatment; Agro OD = 0.1; 5 min inoculation | 80 | 24 | 8 | 10 |
| PEG Treatment; Agro OD = 0.1; 5 min inoculation | 80 | 33 | 14 | 17.5 |

Example 12

This example demonstrates that competency of plant cells can be improved by contacting the plant cells with a medium containing PEG and growth regulators such as auxins. Corn immature embryos were isolated manually as described elsewhere in the present disclosure from inbred line LH 244 and stored in either 1 ml of Lynx 1854 (Table 20), containing 2.2 mg/L picloram 20% PEG 8000 (v/v) or Lynx 1854 without PEG 8000 at 4° C. for 6 days in dark. The embryos were subsequently cultured on callus induction medium Lynx 1074 for about 2 weeks. FIG. 1 illustrates callus production only from the embryos that were stored in Lynx 1854 medium supplemented with PEG and picloram (left panel), compared to embryos that were stored in only Lynx 1854 (right panel).

TABLE 20

Lynx 1854 medium composition

| Ingredient | Source | Amount per liter |
|---|---|---|
| MS Basal Salts | Phytotech M524 | 4.33 g |
| MS Vitamins | Phytotech M533 | 103.1 mg |
| Thiamine HCL | Sigma T-3902 | 0.5 mg |
| 2,4-D | Phytotech D295 | 0.5 mg |
| Sucrose | Phytotech S391 | 30 g |
| Proline | Sigma P-5607 | 1.38 g |
| Casamino Acids | Difco DF0288-17 | 0.5 g |
| Polyethylene Glycol - MW 8000 | Sigma P-2139 | 200 g |
| Picloram | Sigma P-5575 | 2.2 mg |
| pH to 5.8 | | |

Example 13

This example demonstrates improved transformation of corn embryos when they were stored in a medium containing PEG and one or more growth regulators. Corn immature embryos were isolated manually as described elsewhere in the present disclosure from inbred line LH 244 and divided into treatments. Treatment 2 was stored in Lynx 1452 medium (Table 21) supplemented 20% (v/v) PEG 8000, 0.5 mg/l 2,4-D; 0.01 mg/L BAP (Sigma B-3408), while Treatment 3 was stored in Lynx 1452 supplemented with 20% (v/v) PEG, 0.5 mg/l 2,4-D; 2.2 mg/l Picloram. Treatments 2 and 3 were stored for 4 days at 6° C. in dark. For control (treatment 1), embryos were not stored, nor contacted with PEG or any growth regulators prior to transformation. After storage the embryos were inoculated in 1 mL agro culture suspension for 5 minutes, the agro was removed, and then they were once again inoculated with 1 mL agro culture suspension for another 5 minutes. Subsequent culturing and plant regeneration was performed according to the method described in U.S. Pat. No. 7,682,829.

As shown in Table 22, contacting corn embryos with a medium containing PEG and one or more growth regulators resulted in higher transformation frequency.

TABLE 21

Lynx 1452 Medium Composition

| Ingredient | Source | Amount per liter |
|---|---|---|
| MS Basal Salts (Phytotech) | Phytotech M524 | 4.33 g |
| MS Vitamins (100X) (Phytotech) | Phytotech M533 | 103.1 mg |
| Thiamine HCL (Sigma) | Sigma T-3902 | 0.5 mg |
| Sucrose (Phytotech) | Phytotech S391 | 30 g |
| Proline (Sigma) | Sigma P-5607 | 1.38 g |
| Casamino Acids (Difco) | Difco DF0288-17 | 0.5 g |
| pH | | 5.8 |

TABLE 22

Transformation frequency of corn embryos contacted with PEG and various PGRs.

| Treatment | Storage medium | # Embryos to selection medium | # Events produced | % TF |
|---|---|---|---|---|
| 1 (Control) | N/A | 188 | 68 | 36.2 |
| 2 | Lynx 1452 w/20% PEG 8000; 0.5 mg/l 2,4-D; 0.01 mg/L BAP | 269 | 155 | 57.6 |
| 3 | Lynx 1452 w/20% PEG 8000; 0.5mg/l 2,4-D; 2.2 mg/l Picloram | 278 | 144 | 51.8 |

Example 14

This example demonstrates use of PEG alone or PEG in combination with growth regulators to improve competency of plant cells for transformation at different temperatures. Corn immature embryos were isolated manually as described elsewhere in the present disclosure from inbred line LH 244 and stored in either Lynx 2304 containing 20% (v/v) PEG 8000, or stored in Lynx 2304 containing 20% (v/v) PEG 8000 and 0.5 mg/l 2,4-D+0.01 mg/1 BAP. They were stored for 3 days at 4° C. or 23° C. in dark before being transformed according to the method described in U.S. Pat. No. 7,682,829. As shown in Table 23, corn embryos that were stored in a medium of Lynx 2304 plus PEG, or Lynx 2304 plus PEG and growth regulators, at 4° C. or 23° C. produced transgenic plants. Corn embryos that were stored in the medium containing PEG and growth regulators produced more transgenic plants than those stored in the medium containing no BAP. Corn embryos that were stored at 4° C. produced more transgenic plants than embryos that were stored at 23° C.

TABLE 23

Transformation frequency of corn embryos contacted with PEG and PGRs at various temperatures.

| Storage Condition | # Embryos to selection medium | # Events produced | % TF |
|---|---|---|---|
| Lynx 2304 + PEG @ 4 C. (Total of 4 replicates) | 203 | 45 | 22.2 |
| Lynx 2304 + PEG + 2,4-D + BAP @ 4 C. (Total of 4 replicates) | 218 | 59 | 27.1 |
| Lynx 2304 + PEG @ 23 C. (Total of 4 replicates) | 218 | 33 | 15.1 |
| Lynx 2304 + PEG + 2,4-D + BAP @ 23 C. (Total of 4 replicates) | 228 | 47 | 20.6 |

Example 15

This example demonstrates use of PEG in combination with growth regulators to improve competency of plant cells for transformation when embryos were stored for different periods of time. Corn immature embryos were isolated manually as described elsewhere in the present disclosure from inbred line LH 244 and stored in Lynx 2304 containing 20% (v/v) PEG 8000, 0.5 mg/l 2,4-D, 0.01 mg/l BAP for 3, 5, or 7 days at 4° C. in dark. The embryos were then transformed according to the method described in U.S. Pat. No. 7,682,829 As shown in Table 24, corn embryos that were stored either at 3, 5, or 7 produced transgenic plants. Corn embryos that were stored for 3 days produced more transgenic plants than those that were not stored in a medium containing PEG 8000 and growth regulators.

TABLE 24

Transformation frequency of corn embryos contacted with PEG and PGRs, stored for various durations of time.

| Storage period | Storage medium | Embryos to selection medium | Transgenic plants produced | % TF |
|---|---|---|---|---|
| No storage | N/A | 393 | 173 | 44 |
| 3 d | 20% PEG 8000; 0.5 mg/l 2,4-D; 0.01 mg/l BAP | 421 | 203 | 48.2 |
| 5 d | 20% PEG 8000; 0.5 mg/l 2,4-D; 0.01 mg/l BAP | 384 | 137 | 35.7 |
| 7 d | 20% PEG 8000; 0.5 mg/l 2,4-D; 0.01 mg/l BAP | 357 | 58 | 16.2 |

Example 16

This example demonstrates the use of PEG in improving competency of plant cells that were isolated mechanically. Corn embryos were excised mechanically as described in U.S. Pat. No. 7,560,611 and stored in Lynx 2304 containing 20% (v/v) PEG 8000 for 2 days at 4° C. in dark. The embryos were then transformed according to the method described in U.S. Pat. No. 7,682,829. As shown in Table 25, corn embryos that were mechanically excised were able to produce transgenic plants after two days of storage in two different experiments.

TABLE 25

Transformation frequency of mechanically
isolated corn embryos treated with PEG.

| Expt | # Embryos to selection | # Events produced | % TF |
|---|---|---|---|
| 10194 | 133 | 36 | 27.1 |
| 10195 | 120 | 23 | 19.2 |

Example 17

Figure 2:
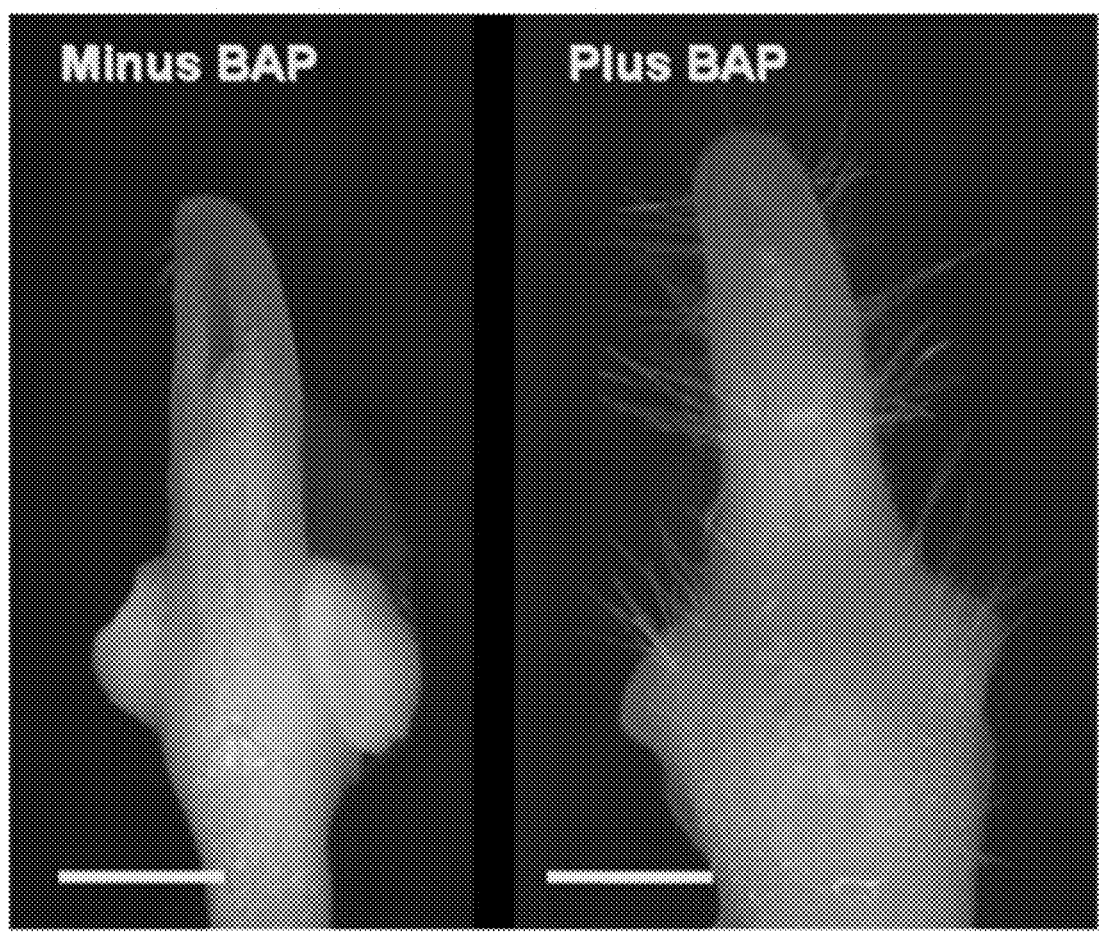
FIG. 2 illustrates enhanced trichome formation and swelling of the coleoptilar node from the embryos that were stored in Lynx 2304 medium supplemented with PEG and BAP (right panel) compared to the embryos that were stored without BAP (left panel).

This example shows that effective delivery of growth regulators to plant cells/tissues can be achieved by contacting the plant cells/tissues with a medium containing PEG and growth regulators such as a cytokinin prior to culturing the plant cells/tissues. Corn immature embryos were isolated manually as described elsewhere in the present disclosure from the inbred line LH 244 and stored in either 1 ml of Lynx 2304 or 1 ml of Lynx 2304 containing 20% PEG 8000 (v/v), 5 mg/l BAP (v/v) at 4° C. for 14 days in dark. The embryo explants were then plated on a germination medium after removal of the PEG. Just prior to plating the embryos stored in Lynx 2304 alone, 5 mg/l BAP (v/v) was added to storage tube. The embryos were subsequently cultured on germination medium Lynx 1607 (Table 26) without any cytokinin for about one week. FIG. 2 illustrates enhanced trichome formation and swelling of the coleoptilar node from the embryos that were stored in Lynx 2304 medium supplemented with PEG and BAP (right panel) compared to the embryos that were stored without BAP (left panel).

TABLE 26

Lynx 1607 medium composition

| Ingredient | Source | Amount per liter |
|---|---|---|
| MS Basal Salts | Phytotech M524 | 4.33 g |
| MS Vitamins | Phytotech M533 | 103.1 mg |
| Sucrose | Phytotech S391 | 60 g |
| Phytagar | Gibco 10695-047 | 6 g |
| Carbenicillin | Phytotech C346 | 100 mg |
| pH | | 5.8 |

Example 18

Figure 3:
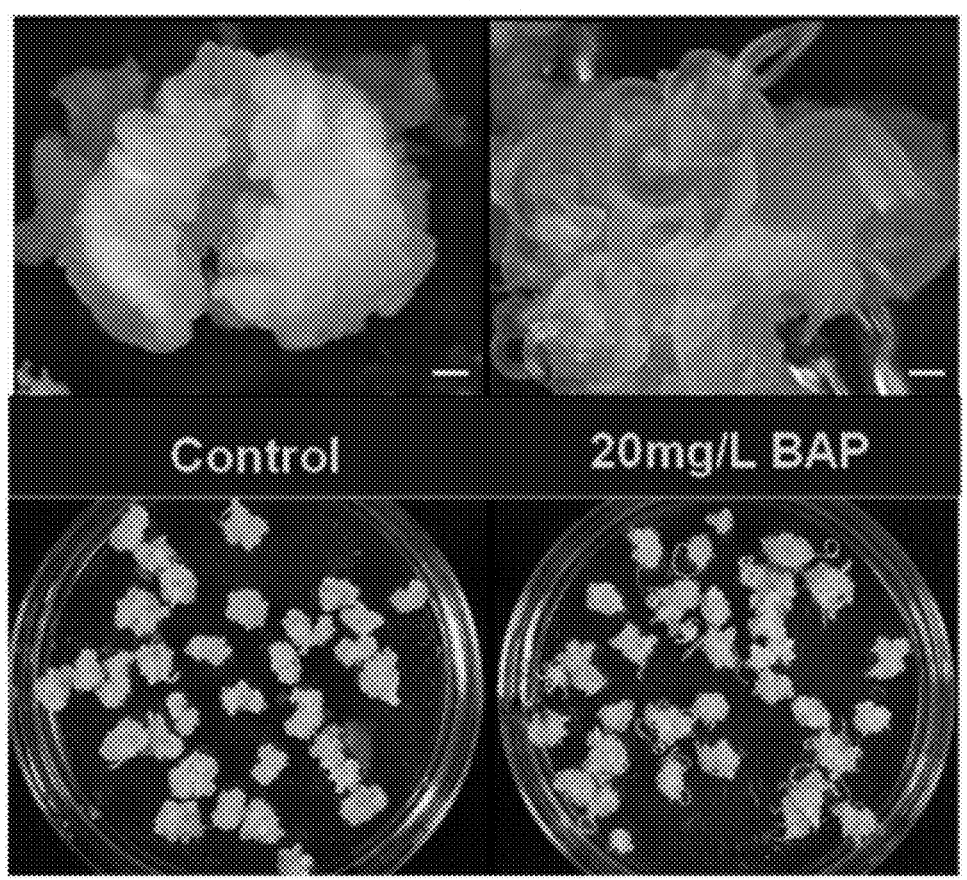
FIG. 3 illustrates improved shoot formation from the embryos that were stored in Lynx 2304 medium supplemented with PEG and BAP (right panel) compared to the embryos that were stored in Lynx2304 medium without BAP (left panel).

This example further demonstrates enhancement of competency of plant cells/tissues by contacting the plant cells/tissues with a medium containing PEG and growth regulators such as a cytokinin. Corn immature embryos were isolated manually as described elsewhere in the present disclosure from the inbred line LH 244 and stored in either 1 ml of Lynx 2304 or 1 ml of Lynx 2304 containing 20% PEG 8000 (v/v) and 20 mg/l BAP (V/v) at 4° C. for 3 days in dark. The embryos were subsequently cultured on callus induction medium Lynx 1074 for about 2 weeks. FIG. 3 shows improved shoot formation from the embryos that were stored in Lynx 2304 medium supplemented with PEG and BAP (top right, bottom right panels) compared to embryos that were stored without PEG or BAP (top left, bottom left panels). Thus, this example also demonstrates enhanced, rapid regeneration of shoot and shoot-like structures from embryogenic callus produced from explants that were contacted with PEG and a cytokinin for an effective period of time prior to culturing on an auxin-containing callus induction medium (Lynx 1074).

Example 19

This example demonstrates the effect of another commonly used cryoprotectant osmoticum, glycerol, compared to PEG, in the storage of embryos. Corn immature embryos were isolated manually as described elsewhere in the present disclosure from the inbred line LH 244. Embryos were transferred to eppendorff tubes containing 1 ml of Lynx 1854, Lynx 1854 with 20% glycerol and no PEG, or Lynx 1854 with both 20% glycerol and 20% PEG. There was one eppendorff tube each media. All of the three tubes were stored at 4 C for 6 days. After this incubation period the tubes were removed from the incubation and the entire contents from each tube were transferred to 1074 semi-solid medium followed by spreading out the immature embryos (20-25/plate). Culture response was scored 7 days after incubating the embryos on 1074 under dark. As shown in Table 27, culture response was only achieved form Treatment #1 with PEG alone. Either glycerol when present alone or in combination with PEG had a negative effect during storage as there was no culture response from scutellar tissues.

TABLE 27

Effect of glycerol on culture response compared to PEG

| Treatment | Culture Response |
|---|---|
| Lynx 1854 (20% v/v PEG 8000) | Yes |
| Lynx 1854 + 20% v/v glycerol, NO PEG | No |
| Lynx 1854 + 20% v/v glycerol and 20% v/v PEG | No |

Example 20

Enhanced Transformation of Cotton Cells Contacted with PEG

This example demonstrates enhanced transformation of dry cotton embryos that were contacted with a composition containing PEG in sterile water. Cotton cv. DP393-0053 seeds were sanitized with 10% Clorox bleach for 10 minutes. They were then dried in a seed dryer overnight, achieving an average internal moisture content of 3.4%. Dry embryos were excised from the dry seeds by first processing the seed through a disc-style grinder, model GP-140 (Modern Process Equipment Corp., Chicago, Ill.), and then processed in an automated sieving and airflow separation device, like the Clipper Eclipse 324 (Clipper Separation Technologies; A. T. Ferrell Company, Bluffton, Ind.) to remove a substantial portion of undesirable seed parts, such as seed coats, dust and other debris. The retained seed material was immersed in liquid nitrogen until it stopped boiling (about 30 seconds), and then processed once again through the disc-style grinder, before being additionally screened to isolate desired embryo explant material from undesired material such as cotyledons, seed coats and other debris, as described in U.S. Patent Application Publication No. 2008/0280361. Dry embryos were contacted for an hour with 20% PEG-4000 dissolved in sterile water. The embryos were rinsed for 4 minutes in RO water, and then subjected to agrobacterium-mediated transformation according to the methods described in U.S. Pat. No. 8,044,260. The embryos were regenerated on a spectinomycin selection medium. As shown in Table 28, embryos contacted with 20% PEG composition generally showed enhanced transformation frequency, compared to embryos contacted with INO medium (with no PEG). See Table 29 for spectinomycin selection medium composition for cotton.

TABLE 28

Transformation frequency of cotton cells contacted with PEG in water compared to INO medium

| Treatment | Initial Explants | #R0 Plants | TF % (stdev) |
|---|---|---|---|
| INO | 10000 | 140 | 1.4% (.26) |
| 20% PEG4000 in water | 5000 | 120 | 2.4% (.38) |

TABLE 29

Spectinomycin selection medium composition for cotton.

| Ingredient | Source | Amount per liter |
|---|---|---|
| Gamborg's B5 Medium | Phytotech G398 | 3.21 g |
| Dextrose | Fisher D16-3 | 20 g |
| Calcium Gluconate | Sigma G-4625 | 1.29 g |
| Clearys 3336 WP | Carlin 10-032 | 0.03 g |
| Agargel | Sigma A-3301 | 4 g |
| Carbenicillin (40 mg/mL stock) | Phytotech C346 | 5 mL |
| Timentin (100 mg/mL stock) | Duchefa T0190 | 1 mL |
| Cefotaxime (50 mg/mL stock) | Midwest NDC0039-0019-10 | 4 mL |
| Spectinomycin (50 mg/mL stock) | Sigma S-4014 | 5 mL |

The invention claimed is:

1. A method for improving competency of plant embryo cells for bacterial-mediated transformation comprising:
    (a) contacting a mature plant embryo explant with an effective amount of a polyethylene glycol (PEG) containing composition having from about 10% to about 50% by volume of polyethylene glycol; and
    (b) transforming at least one cell of the mature plant embryo explant with a heterologous DNA sequence via bacterial-mediated transformation,
    wherein the transforming step (b) is performed after the contacting the step (a); wherein the PEG containing composition is removed prior to the transforming step (b); wherein the mature plant embryo explant is excised from a dry seed; and wherein the improved competency is measured as an increase in transformation frequency.

2. The method of claim 1, wherein the at least one transformed cell of the mature plant embryo explant is a meristematic cell.

3. The method of claim 1, wherein the mature plant embryo explant is from a soybean or cotton seed.

4. The method of claim 1, wherein the PEG containing composition is removed by rinsing the mature plant embryo explant with a non-PEG containing composition prior to the transforming step (b).

5. The method of claim 1, wherein the PEG containing composition in the contacting step (a) has from about 10% to about 25% by volume of polyethylene glycol.

6. The method of claim 1, wherein the bacterial-mediated transformation is *Agrobacterium*-mediated, *Rhizobium*-mediated, *Sinorhizobium*-mediated, *Mesorhizobium*-mediated, or *Bradyrhizobium*-mediated transformation.

7. The method of claim 6, wherein the bacterial-mediated transformation is *Agrobacterium*-mediated transformation.

8. The method of claim 1, wherein the transforming step (b) is performed without any prior callus induction of the mature plant embryo explant.

* * * * *